US009486519B2

(12) United States Patent
Sahin et al.

(10) Patent No.: US 9,486,519 B2
(45) Date of Patent: Nov. 8, 2016

(54) USE OF FLT3 LIGAND FOR ENHANCING IMMUNE RESPONSES IN RNA IMMUNIZATION

(75) Inventors: Ugur Sahin, Mainz (DE); Özlem Türeci, Mainz (DE); Sebastian Kreiter, Mainz (DE); Abderraouf Selmi, Mainz (DE)

(73) Assignees: BioNTech AG, Mainz (DE); TRON—Translationale Onkologie an der Universitätsmedizin der Johannes Gutenberg—Universität Mainz gemeinnützige GmbH, Mainz (DE)

( * ) Notice: Subject to any disclaimer, the term of this patent is extended or adjusted under 35 U.S.C. 154(b) by 619 days.

(21) Appl. No.: 13/139,034

(22) PCT Filed: Dec. 9, 2009

(86) PCT No.: PCT/EP2009/008811
§ 371 (c)(1),
(2), (4) Date: Sep. 2, 2011

(87) PCT Pub. No.: WO2010/066418
PCT Pub. Date: Jun. 17, 2010

(65) Prior Publication Data
US 2011/0311584 A1    Dec. 22, 2011

(30) Foreign Application Priority Data
Dec. 10, 2008   (DE) ......................... 10 2008 061 522

(51) Int. Cl.
A61K 48/00      (2006.01)
A61K 39/39      (2006.01)
C07K 14/475     (2006.01)
A61K 39/00      (2006.01)

(52) U.S. Cl.
CPC ............. *A61K 39/39* (2013.01); *C07K 14/475* (2013.01); *A61K 2039/53* (2013.01); *A61K 2039/55516* (2013.01); *C07K 2319/00* (2013.01)

(58) Field of Classification Search
CPC .......... C07K 2319/00; C07K 2319/30; A61K 39/0011; A61K 2300/00; A61K 39/00; A61K 2039/53; A61K 38/00; A61K 39/39; A61K 2039/5154; A61K 2039/55511; A61K 2039/57; A61K 2039/55516
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,837,028 A | 6/1989 | Allen | |
| 5,019,369 A | 5/1991 | Presant et al. | |
| 5,554,512 A | 9/1996 | Lyman et al. | |
| 6,291,661 B1 | 9/2001 | Graddis et al. | |
| 7,005,131 B1 | 2/2006 | Steinman | |
| 2008/0199485 A1* | 8/2008 | Kundig et al. ............. | 424/184.1 |

FOREIGN PATENT DOCUMENTS

| WO | 02061113 A2 | 8/2002 |
|---|---|---|
| WO | WO 02/061113 A2 | 8/2002 |
| WO | 2005052119 A2 | 6/2005 |
| WO | WO 2005/052119 A2 | 6/2005 |
| WO | 2007/036366 A2 | 4/2007 |

OTHER PUBLICATIONS

Mach et al, Cancer Res, 2000, 60:3239-3246.*
Pascolo, Methods Mol Med, 2006, 127:23-40, Abstract.*
Carralot et al., "Polarization of immunity induced by direct injections of naked sequence-stabilized mRNA vaccines", CMLS, Cell. Mol. Life Sci. 61, 2004, pp. 2418-2424, XP-002355208.
Chavan et al., "Expression of CCL20 and granulocyte-macrophage colony-stimulating factor, but not Flt3-L, from modified vaccinia virus Ankara enhances antiviral cellular and humoral immune responses", Journal of Virology, vol. 80, No. 15, Aug. 2006, pp. 7676-7687, XP-002571845.
Xu et al., "Recombinant DNA vaccine of the early secreted antigen ESAT-6 by *Mycobacterium tuberculosis* and Flt3 ligand enhanced the cell-mediated immunity in mice", Vaccine 26, 2008, pp. 4519-4524, XP-002571844.
Surgery, 2003, vol. 134, No. 2, p. 300-305.
Journal of Surgical Research, 2004, vol. 116, No. 1, p. 24-31.
Cancer Gene Therapy, 2003, vol. 10, No. 9, p. 696-706.
Journal of Immunology, 1999, vol. 163, No. 3, p. 1289-1297.
Oncology Reports, Feb. 2008, vol. 19, No. 2, p. 505-515.
Journal of Immunotherapy, 2006, vol. 29, No. 5, p. 499-511.
Shimonkevitz, R. et al., 1983, J. Exp. Med. 158:303.
Smith and Waterman, 1981, Ads App. Math. 2, 482.
Speiser, D.E. et al. (2005) Journal of Clinical Investigation 115:739-746.
Spooner, R.A. et al. (1995) Gene Ther. 2:173-180.
Steimnan, R.M., AIIDU. Rev.Immunol., 9:271-296 (1991).
Strong, T. V., et al., Gene Ther. vol. 4, No. 6, Jun. 1997, pp. 624-627, XP009012148.
Su, Z. (2003) Cancer Res. 63:2127-2133.
Szoka et al. (1980), Ann. Rev. Biophys. Bioeng. 9: 467.
Tang, D.C. et al. (1992) Nature 356:152-154.
Tanguay R. L. et al.: Mol. Cell. Biology, Amer. Soc. For Microb. vol. 16, No. 1, 1996, pp. 146-156 XP002370890.
Teufel, R., et al., CMLS Cell. and Mol. Life Sci., vol. 62, No. 15, Aug. 2005, pp. 1755-1762, XP002392461.
Ulmer, J.B. (1993) Science 259:1745-1749.
Wang, B. et al. (1993) Proc. Natl. Acad. Sci. U.S.A. 90:4156-4160.
Wang, B. et al. (1995) Hum. Gene Ther. 6:407-418.
Weide, B. (2008).
Ying, H. et al. (1999) Nat. Med. 5:823-827.
Int'l Search Report for PCT/EP2009/008811 dated Mar. 26, 2010.
Aguilar, J.C. et al. (2007) Vaccine 25:3752-3762.
Bargmann, C.I. et al. (1986) Nature 319:226-230.
Bellone et al., J. Immunol., 2000, 165:2651-2656.

(Continued)

*Primary Examiner* — Marcia S Noble
(74) *Attorney, Agent, or Firm* — McAndrews, Held & Malloy, Ltd.

(57) ABSTRACT

The invention relates to supplying vaccine RNA to cells. The invention relates in particular to a common use of vaccine RNA and Flt3 ligand for inducing, creating or enhancing an immune response when administered to animals (including humans).

6 Claims, 11 Drawing Sheets

(56) References Cited

OTHER PUBLICATIONS

Boczkowskid et al., Cancer Res., Amer. Assoc. For Cancer Res., vol. 60, Feb. 15, 2000, pp. 1028-1034, XP001048606.
Bontkes, H.J. et al. (2007) Gene Therapy 14:366-375.
Chiarella, P. et al. (2007) Expert Opinion on Biological Therapy 7:1551-1562.
Condon, C. et al. (1996) Nat. Med. 2:1122-1128.
Conry, R.M. et al. (1994) Cancer Res. 54:1164-1168.
Conry, R.M. et al. (1995) Gene Ther. 2:59-65.
Conry, R.M. (1995) Cancer Research 55:1397-1400.
Cox, G.J. et al. (1993) J. Virol. 67:5664-5667.
Cui, Z.R. et al. (2006) Cancer Immunology Immunotherapy 55:1267-1279.
Dannull, J. et al. (2005) Blood 105:3206-3213.
Davis, H.L. et al. (1993) Hum. Mol. Genet. 2:1847-1851.
Freedman, R.S. et al. (2003) Clinical Cancer Research 9:5228-5237.
Gallie, D.R., Gene, vol. 216, No. 1, Aug. 1998, pp. 1-11, XP004149275.
Gilkeson, G.S. et al. (1995) J. Clin. Invest. 95:1398-1402.
Granstein, R.D. et al. (2000) Journal of Investigative Dermatology 114:632-636.
Greenblatt, M.S. et al. (1994) Cancer Res. 54:4855-4878.
Grunebach, F. (2005) Cancer Gene Therapy 12:749-756.
Guhaniyogi, J. et al., Gene. vol. 265, No. 1-2, Mar. 7, 2001, pp. 11-23, XP004230718.
Hannum, C. et al. (1994) Nature 368:643-648.
Heiser, A. (2000) J. Immunol. 164:5508-5514.
Heiser, A. et al. (2002) J. Clininvest. 109:409-417.
Hoerr, I. et al. (2000) Eur. J. Immunol. 30:1-7.
Holtkamp Silke, et al., Blood, vol. 108, No. 13, Dec. 15, 2006, pp. 4009-4017, XP002418545.
Inaba, Kayo, Biotherapy (Tokyo), 2000, vol. 14, No. 12, p. 1161-1168, ABS only; rest not in English.
IPRP for Application No. PCT/EP2006/009448 dated Apr. 1, 2008.
Jaffee, E.M. (2001) Journal of Clinical Oncology 19:145-156.
Li, X., et al., Journ. of Biol. Chem. Amer. Soc. of Biolochem. Biolog., vol. 271, No. 52, pp. 24970-34975, Dec. 25, 1998, XP000984126.
Lyman, S.D. et aL (1994) Blood 83:2795-2801.
Maraskovsky, E. et al. (1996) Journal of Experimental Medicine 184:1953-1962.
Maraskovsky, E. et al. (2000) Blood 96:878-884.
McNeel, D.G. et al. (2003) Journal of Clinical Immunology 23:62-72.
Michiels, A. (2006) Gene Therapy 13:1027-1036.
Mignone, F., et al., Genome Biology, vol. 3, No. 3, 2002, pp. 0004.1-0004.10, XP002428984.
Neddleman and Wunsch, 1970, J. Mol. Biol. 48, 443.
Neidhart, J. et al. (2004) Vaccine 22:773-780.
Pearson and Lipman, 1988, Proc. Natl Acad. Sci. USA 85, 2444.
Pesole, G., et al., Gene, vol. 276, No. 1-2, pp. 73-81, Oct. 3, 2001, XP004308679.
Preiss, T., et al., Nature, vol. 392, No. 6675, pp. 516-520, Apr. 2, 1998, XP002240279.
Rains, N. (2001) Hepato-Gastroenterology 48:347-351.
Robinson et al., 2003, BMT, 31 :361-369.
Sambrook et al. Molecular Cloning: A Laboratory Manual, 2nd Edition, Cold Spring Harbor Laboratory press, Cold Spring Harbor, New York, 1989 Ausubel et al., Current Protocols in Molecular Biology, Editors, John Wiley & Sons, Inc., New York.
Science 268:1432-1434, 1995.
Shackleton M. et al. (2004) Cancer Immunity 4:9-20.
Fong, et al., Dendritic Cells Injected Via Different Routes Induce Immunity in Cancer Patients, Journal of Immunology, 2001, vol. 166, No. 6, p. 4254-4259.
Chang, et al., A Pilot Clinical Trial of Vaccination with Dendritic Cells Pulsed with Autologous Tumor Cells Derived from Malignant Pleural Effusion in Patients with Late-Stage Lung Carcinoma, American Cancer Society, 2005, vol. 103, No. 4, p. 763-771.
Boczkowski, et al., Dendritic Cells Pulsed with RNA are Poitent Antigen-presenting Cells in Vitro and In Vivo, Journal of Experimental Medicine, 1996, vol. 184, No. 2, p. 465-472.
Lynch, et al., Flt3 ligand induces tumor regression and antitumor immune responses in vivo, Nature Medicine, 1997, vol. 3, No. 6, p. 625-631.

* cited by examiner

USE OF FLT3 LIGAND FOR ENHANCING IMMUNE RESPONSES IN RNA IMMUNIZATION

The invention relates to the area of vaccination and immunostimulation through the use of RNA, in particular mRNA, that codes for one or more antigens, which are associated for example with infectious diseases or malignant diseases such as cancer.

The immune system can display both specific and non-specific immunity. In general, specific immunity is produced by B and T lymphocytes, which have, on their cell surface, specific receptors for a particular antigen. The immune system can react to different antigens in two different ways: (i) humoral immunity, which includes B cell stimulation and production of antibodies or immunoglobulins, and (ii) cell-mediated immunity, which generally includes T cells, including cytotoxic T lymphocytes (CTL).

Antigen-specific T cell reactions are brought about by antigenic peptides, which are bound to the binding groove of glycoproteins of the major histocompatibility complex (MHC), as part of the mechanism of the immune system by which foreign antigens are identified and a reaction is triggered against them. The bound antigenic peptides interact with T cell receptors and thus modulate an immune response. The antigenic peptides are bound noncovalently to particular "binding pockets", which are formed from polymorphic residues of the binding groove of the MHC protein.

MHC class II molecules are heterodimeric glycoproteins, which consist of α and β chains. The α1 and β1 domains of these molecules fold together and form a peptide-binding groove. Antigenic peptides bind to the MHC molecule by interaction between anchor amino acids on the peptide and the α1 and β1 domains. MHC class I molecules possess different domain organizations than MHC class II molecules, but generally a similar structure with a peptide-binding site or groove, which is remote from the membrane domains.

The initial step in the presentation of a foreign protein-antigen is the binding of the native antigen to an antigen-presenting cell (APC). After binding to APCs, antigens penetrate into the cells, either by phagocytosis, receptor-mediated endocytosis or pinocytosis. These internalized antigens are localized in intracellular membrane-bound vesicles, called endosomes. After endosome-lysosome fusion, the antigens are processed to small peptides by cellular proteases located in the lysosomes. The peptides associate with the α and β chains of MHC class II molecules within these lysosomes. These MHC class II molecules, which had been synthesized beforehand in the rough endoplasmic reticulum, are transported sequentially to the Golgi complexes and then to the lysosomal compartment. The peptide-MHC complex is presented on the surface of APCs for T and B cell activation.

Non-specific immunity comprises various cells and mechanisms such as phagocytosis by macrophages or granulocytes and activity of natural killer cells (NK). Nonspecific immunity is based on mechanisms that have not advanced so far in evolutionary terms, and does not have the properties with respect to specificity and memory capacity that are important features of a specific immune response.

Recombinant vaccines are especially important in human and veterinary medicine as active substances and medicinal products for the prophylaxis and treatment of infectious diseases and cancers. The aim of vaccination with a recombinant vaccine is to induce a specific immune response to a defined antigen, providing a preventive or therapeutic effect against defined diseases.

After it was shown that the direct intramuscular injection of plasmid-DNA leads to long-lasting expression of the encoded genes on the cell surface (Wolff, J.-A. et al. (1990) Science 247:1465-1468), DNA-based vaccines appeared as a promising new immunization strategy. These observations were an important incentive to develop nucleic acid-based vaccines. First, DNA-based vaccines were tried against infectious pathogens (Cox, G. J. et al. (1993) J. Virol. 67:5664-5667, Davis, H. L. et al. (1993) Hum. Mol. Genet. 2:1847-1851, Ulmer, J. B. (1993) Science 259:1745-1749, Wang, B. et al. (1993) Proc. Natl. Acad. Sci. U.S.A. 90:4156-4160), but soon research was also conducted into gene therapy against tumors, in order to induce a specific antitumor immunity (Conry, R.-M. et al. (1994) Cancer Res. 54:1164-1168, Conry, R. M. et al. (1995) Gene Ther. 2:59-65, Spooner, R. A. et al. (1995) Gene Ther. 2:173-180, Wang, B. et al. (1995) Hum. Gene Ther. 6:407-418). This strategy of tumor immunization has a number of decisive advantages. Nucleic acid-based vaccines are simple to manufacture and relatively inexpensive. Moreover, they can be amplified from a small number of cells.

DNA is more stable than RNA but involves some potential safety risks such as induction of anti-DNA antibodies (Gilkeson, G. S. et al. (1995) J. Clin. Invest. 95:1398-1402) and integration of the transgene into the host genome. That can lead to inactivation of cellular genes, an uncontrollable long-term expression of the transgene, or oncogenesis, and therefore cannot generally be used for tumor-associated antigens with oncogenic potential such as e.g. erb-B2 (Bargmann, C. I. et al. (1986) Nature 319:226-230) and p53 (Greenblatt, M. S. et al. (1994) Cancer Res. 54:4855-4878). To avoid these potential risks, the use of RNA offers an attractive alternative.

The advantages of RNA as a form of reversible gene therapy include temporary expression and the non-transforming character. RNA does not need to enter the nucleus in order to be expressed transgenically and moreover cannot be integrated into the host genome, so that the risk of oncogenesis is eliminated. As with DNA (Condon, C. et al. (1996) Nat. Med. 2:1122-1128, Tang, D. C. et al. (1992) Nature 356:152-154), both the cellular and the humoral immune response can also be induced in vivo by injection of RNA (Hoerr, I. et al. (2000) Eur. J. Immunol. 30:1-7, Ying, H. et al. (1999) Nat. Med. 5:823-827).

For immunotherapy with in-vitro transcribed (IVT-RNA) or in-vitro amplified RNA, two different strategies are pursued, both of which have been tested successfully in various animal models and have found preliminary application in humans.

Either dendritic cells (DCs) are transfected with the in-vitro transcribed RNA by lipofection or electroporation and then applied (Heiser, A. (2000) J. Immunol. 164:5508-5514) or the RNA is injected directly via various immunization routes (Hoerr, I. et al. (2000) Eur. J. Immunol. 30:1-7, Granstein, R. D. et al. (2000) Journal of Investigative Dermatology 114:632-636, Conry, R. M. (1995) Cancer Research 55:1397-1400). It was shown that immunization with RNA-transfected DCs induces antigen-specific CTLs in vitro and in vivo (Su, Z. (2003) Cancer Res. 63:2127-2133, Heiser, A. et al. (2002) J. Clin. Invest. 109:409-417). Preliminary clinical data on the use of RNA-transfected dendritic cells as tumor vaccine date back to the years 2001 and 2002 and showed that antigen-specific T cells can be induced in tumor patients (Heiser, A. et al. (2002) J. Clin.

Invest. 109:409-417, Rains, N. (2001) Hepato-Gastroenterology 48:347-351). For the direct intradermal injection of RNA in patients, in the meantime the preliminary data of a phase I/II clinical study in melanoma patients are now available (Weide, B. (2008) Journal of Immunotherapy 31:180-188). This demonstrated the safety and low toxicity of injection of naked RNA. On the basis of preclinical data, which had shown improved TH-1 immunity after GM-CSF administration, GM-CSF was used as adjuvant (Carralot, J.-P. et al. (2004) Cell Mol. Life. Sci. 61:2418-2424). However, no clinical effects were observed in the melanoma patients treated.

RNA vaccines can therefore be used for transiently transfecting cells with RNAs that code for protein antigens, expression of which stimulates an immune response. Based on the intracellular production of these antigens and processing thereof over the endogenous pathway, RNA vaccines induce humoral immunity, and T cell immunity with production of cytotoxic T lymphocytes (CTLs).

Based on the properties described above, RNA seems especially suitable for clinical applications. The use of RNA is, however, greatly restricted mainly by the short half-life of RNA in the cytoplasm, as the molecule is quickly degraded by enzymes, with the result that there is little protein expression. Therefore it is of considerable interest to amplify the immunogenicity of RNA as active substance.

Adjuvants have long been used for potentiating the action of vaccinations (Aguilar, J. C. et al. (2007) Vaccine 25:3752-3762, Chiarella, P. et al. (2007) Expert Opinion on Biological Therapy 7:1551-1562). A great variety of agents such as CpG, Poly I:C, GM-CSF, Flt3 ligand or monophosphoryl lipid A have already been investigated in preclinical and early-stage clinical studies with respect to their potency within the scope of tumor vaccination strategies (Speiser, D. E. et al. (2005) Journal of Clinical investigation 115:739-746, Cui, Z. R. et al. (2006) Cancer Immunology Immunotherapy 55:1267-1279, Jaffee, E. M. (2001) Journal of Clinical Oncology 19:145-156. Shackleton M. et al. (2004) Cancer Immunity 4:9-20, Neidhart, J. et al. (2004) Vaccine 22:773-780). For enhancing immune responses after vaccination with RNA-transfected dendritic cells, in preclinical studies various adjuvants (IL-12, CD40-L, OX40-L, 4-1BBL) were cotransfected (Dannull, J. et al. (2005) Blood 105:3206-3213, Bontkes, H. J. et al. (2007) Gene Therapy 14:366-375, Grunebach, F. (2005) Cancer Gene Therapy 12:749-756). Alternatively, double-stranded RNA (Poly I:C) was also cotransfected with the antigen-coding RNA (Michiels, A. (2006) Gene Therapy 13:1027-1036).

Within the scope of investigations into the use of adjuvants in the context of vaccination with naked IVT-RNA, so far only the s.c. administration of GM-CSF has been tested, which in preclinical investigations led to a slightly enhanced induction of TH-1 immunity (Carralot, J. P. (2004) Cell Mol. Life. Sci. 61:2418-2424). The requirements on adjuvants for use within the scope of direct application of naked RNA differ fundamentally from those for adjuvants that are used within the scope of peptide-, DNA- or cell-based vaccines. This can be explained by the mechanism responsible for the uptake of RNA from the extracellular space in cells.

There is therefore a demand for agents that intensify the degree of immunostimulation when RNA vaccines are administered.

This problem is solved according to the invention by the object of the patent claims.

The invention meets these needs in that it describes compounds that can support uptake of RNA into the cytosol of antigen-presenting cells and/or can produce a more effective immune response on administration of a vaccine-RNA.

The inventors found that administration of RNA molecules that code for antigens that can be used for vaccination and therapy, in conjunction with administration of Flt3 ligand (Flt3-L) can lead effectively to an immune response which is specific to these antigens.

It was found according to the invention that various known adjuvants not only lead to no increase in T cell priming efficiency after direct immunization with naked IVT-RNA, but tend to reduce the T cell response. This finding was surprising and can only be explained by the influence of the adjuvants on RNA uptake in antigen-presenting cells. This is a mechanism which, in a manner described by the inventors for the first time, is responsible for the uptake of long-chain ribonucleic acids. The efficiency of this uptake mechanism is inhibited by various adjuvants. Only Flt3 ligand was able to show a significant adjuvant effect in RNA immunization. The investigations presented here show in particular that when Flt3 ligand was administered together with RNA that codes for an antigen, a strong increase in antigen-specific CD8+ T cells was observed.

The invention relates generally to supplying vaccine-RNA to cells. In particular the invention relates to the joint use of vaccine-RNA and Flt3 ligand for the induction, production or enhancement of an immune response when administered to animals (including humans).

According to the invention, Flt3 ligand—preferably when used with an RNA vaccine—enhances an animal's immune response to specific antigens that are produced by the use of the RNA vaccine. Typical vaccines used in this approach are viral vaccines such as influenza, herpes, cytomegalovirus, HIV-1, HTLV-1 and FIV vaccines, bacterial vaccines, cancer vaccines and vaccines against parasites.

Preferably, according to the invention, an animal is immunized by introducing Flt3 ligand and RNA that codes for an antigen, into an animal. The RNA is taken up into the animal's antigen-presenting cells (monocytes, macrophages, dendritic cells or other cells). An antigenic translation product of the RNA is formed and the product is optionally processed and presented by the cells in the context of major histocompatibility complexes, thus generating an immune response to the antigen. The RNA thus produces the antigen in a translation.

In particular embodiments, the Flt3 ligand is administered before, simultaneously with and/or after administration of an RNA vaccine. Preferably the Flt3 ligand is administered before administration of an RNA vaccine.

In one aspect the invention relates to an immunogenic preparation, which comprises RNA that codes for at least one antigen, and Flt3 ligand. The RNA and the Flt3 ligand can be present in the immunogenic preparation according to the invention in a common composition, i.e. mixed together. Moreover, embodiments are also envisaged according to the invention in which the RNA and the Flt3 ligand are present together, but not in the same composition. Said embodiments relate in particular to kits with at least two containers, where one container contains a composition comprising the RNA, and another container contains a composition comprising the Flt3 ligand.

In the immunogenic preparation according to the invention the RNA is preferably mRNA. The RNA is preferably obtained by in-vitro transcription.

The immunogenic preparation according to the invention can further comprise at least one RNA-stabilizing factor such as an RNase inhibitor for stabilizing the RNA.

The immunogenic preparation according to the invention is preferably a preparation that is formulated for a therapeutic use. According to the invention, the term "therapeutic use" comprises a treatment or prevention of a disease. In this aspect the invention relates to a pharmaceutical composition that comprises an immunogenic preparation according to the invention.

Typically the immunogenic preparation according to the invention or the pharmaceutical composition according to the invention can further comprise a solvent such as an aqueous solvent or any solvent that makes it possible to preserve the integrity of the RNA, an adjuvant such as aluminum hydroxide, Freund's adjuvant, oligonucleotides with a CpG motif or any other adjuvant that is known by a person skilled in the art, and any stabilizer, such as protamine. A pharmaceutical composition according to the invention preferably comprises a pharmaceutically compatible diluent and/or a pharmaceutically compatible excipient.

It is moreover possible to increase the immunogenicity of the preparations according to the invention by adding one or more further adjuvants. It is also possible to stabilize the RNA of the immunogenic preparation according to the invention by complexation with cationic compounds, preferably polycationic compounds such as for example a cationic or polycationic peptide or protein. According to a preferred embodiment of the immunogenic preparation according to the invention the RNA-complexing peptide or protein is a protamine, a poly-L-lysine, a poly-L-arginine or a histone.

A pharmaceutical composition according to the invention is preferably in a form that makes it suitable for vaccination of an organism.

An immunogenic preparation according to the invention or a pharmaceutical composition according to the invention or at least the RNA-comprising component thereof is preferably in the form of a formulation for intranodal administration.

The preparations and compositions described above can be used in the methods, in particular immunization methods, described herein.

In another aspect the invention relates to a method of supplying at least one antigen to cells, which comprises contacting the cells with RNA, which codes for the at least one antigen, and Flt3 ligand. Preferably the cells are in vivo in an organism and the method comprises the administration of the RNA and of the Flt3 ligand to the organism. In a preferred embodiment the cells are antigen-presenting cells, more preferably professional antigen-presenting cells, in particular dendritic cells, monocytes or macrophages.

In this aspect the invention also relates to a method of increasing the amount of MHC/peptide complex in a cell, preferably an antigen-presenting cell, more preferably a professional antigen-presenting cell, in particular a dendritic cell, a monocyte or a macrophage, wherein the method comprises contacting the cell with RNA that codes for the peptide or an expression product that comprises the peptide, and administration of Flt3 ligand. The expression product that comprises the peptide can be processed by the cell preferably to the peptide.

Preferably the method takes place in vivo and the increase in the amount of MHC/peptide complex for its part intensifies the primary activation of T cells, in particular of CD4+ and CD8+ lymphocytes.

In another aspect the invention relates to a method of producing or enhancing an immune response in an individual, which comprises administration of RNA that codes for an antigen, against which the immune response is to be directed, and administration of Flt3 ligand. The immune response preferably has a protective and/or therapeutic action on the individual and preferably comprises an antigen-specific T cell immune response.

In another aspect the invention relates to a method of increasing the amount of antigen-specific effector cells, in particular CD8+ cytotoxic T cells and/or CD4+ helper T cells in an individual, which comprises administration of RNA that codes for the antigen, and administration of Flt-3 ligand.

Another aspect relates to prevention and/or treatment of cancer using an immunization protocol, which includes the use of Flt3 ligand. In this aspect the invention relates in particular to a method for prevention and/or treatment of cancer in an individual, which comprises administration of RNA that codes for a tumor antigen, against which the immune response is to be directed, and administration of Flt3 ligand.

Another aspect relates to prevention and/or treatment of viral infections using an immunization protocol that includes the use of Flt3 ligand. In this aspect the invention relates in particular to a method for prevention and/or treatment of a viral infection in an individual, which comprises administration of RNA that codes for a viral antigen, against which the immune response is to be directed, and administration of Flt3 ligand.

Another aspect relates to prevention and/or treatment of bacterial infections using an immunization protocol that includes the use of Flt3 ligand. In this aspect the invention relates in particular to a method for prevention and/or treatment of a bacterial infection in an individual, which comprises administration of RNA that codes for a bacterial antigen, against which the immune response is to be directed, and administration of Flt3 ligand.

Another aspect relates to prevention and/or treatment of an infection by unicellular organisms using an immunization protocol that includes the use of Flt3 ligand. In this aspect the invention relates in particular to a method of prevention and/or treatment of an infection by a unicellular organism in an individual, which comprises administration of RNA that codes for an antigen of the unicellular organism, against which the immune response is to be directed, and administration of Flt3 ligand.

Another aspect relates to prevention and/or treatment of allergy in a patient, which includes administration of Flt3 ligand together with an allergen-specific immunotherapy. In this aspect the invention relates in particular to a method for prevention and/or treatment of an allergy in an individual, which comprises administration of RNA that codes for an allergen relevant to the allergy, and administration of Flt3 ligand.

Another aspect relates to immunization protocols that include the use of Flt3 ligand, in which the efficacy of vaccines, immunogenicity of antigens or a protective immune response to an antigen and/or a vaccine is tested and assessed in a test organism.

Advantages of treatment and/or prevention of diseases or infections using the strategy described herein include, among other things, that the immunogenicity of weakly immunogenic antigens such as recombinant antigens can be increased, the amount of antigen used or RNA encoding it can be reduced, there is less need for booster immunizations, and the efficiency of immunization is increased.

The use of Flt3 ligand with RNA vaccines can enhance the immunogenicity of certain viral proteins and cancer-specific antigens, which normally produce a weak immune response. The vaccination technique can be used for example for induction of an immune response to weakly immunogenic viral proteins. In the case of the RNA vaccines according to the invention, the protein antigen is never exposed to serum antibodies, but is produced by transfected cells themselves after translation of the mRNA. Therefore anaphylaxis should not be a problem. The invention therefore permits the repeated immunization of a patient without risk of allergic reactions.

The immunization strategy according to the invention also makes possible the quantitative increase in frequency of antigen-specific T lymphocytes after RNA-based immunization. This increase in efficiency can be utilized for the immunotherapy of patients in the sense of better clinical efficacy or in the sense of reduction of the vaccine dose or application frequency with equal efficacy.

In HLA-transgenic mice, by immunization according to the invention with an RNA vaccine that codes for human tumor-associated antigens, T cell clones or T cell receptors can be isolated, which recognize naturally processed epitopes in the context of a human HLA-molecule. By means of the immunization strategy according to the invention, antigen-specific T cells can be generated with a higher probability. Furthermore, the immunization strategy according to the invention offers the possibility of also strongly amplifying antigen-specific T cells that are present at a low precursor frequency. This increase in efficiency permits more comprehensive isolation of the antigen-specific T cells present in the naive repertoire. Furthermore, the increase in efficiency with the immunization method described is associated with a cost reduction.

It is also envisaged, according to the invention, to remove cells from an animal and transfect the cells in vitro with Flt3 ligand/RNA. The RNA is incorporated in the cells and an antigenic translation product of the polynucleotide is formed. After transfection, the cells that express the antigen are introduced into the animal preferably by injection, where the immune system can now react to the antigen, which is now endogenous, and an immune response to the immunogen is produced. In this embodiment according to the invention, the cells to be transfected are preferably lymphoid cells, in particular antigen-presenting cells, which were taken from the animal.

If cells from an animal are to be transfected in vitro, the source of cells can be peripheral blood cells, which can be isolated quickly from whole blood, in order to provide a source for cells that contain both class I and class II MHC molecules. These cells can be fractionated further into B cells, helper T cells, cytotoxic T cells or macrophages/monocytes. Bone marrow cells can provide a source of less differentiated lymphoid cells.

In another aspect, according to the invention a method is provided for stimulation or activation of T cells, in particular $CD4^+$ and $CD8^+$ lymphocytes, in vitro or in an organism, wherein the method comprises the provision, for the T cells or administration to the organism, of RNA that codes for at least one antigen, to which the T cells should be specific, and Flt3 ligand. Said stimulation or activation is preferably manifested in expansion, cytotoxic reactivity and/or cytokine release of the T cells.

The methods described above are suitable in particular for treatment or prophylaxis of infectious diseases, caused for example by bacteria or viruses. In certain embodiments, the antigen used according to the invention is derived from an infectious pathogen such as hepatitis A, B, C, HIV, mycobacteria, malaria pathogens, pathogens of SARS, herpesvirus, influenzavirus, poliovirus or from bacterial pathogens such as chlamydiae and mycobacteria. An especially useful application of the present invention is cancer immunotherapy or vaccination, where in particular activation of tumor antigen-reactive T cells is intensified, so that the prospects for T cell immunotherapy or vaccination against tumor cells are improved.

In specific embodiments, the antigen used according to the invention is selected from the group comprising the following antigens: p53 ART-4, BAGE, ss-Catenin/m, Bcr-abL CAMEL, CAP-1, CASP-8, CDC27/m, CDK4/m, CEA, CLAUDIN-6, CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11 or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor bcr-abL Pml/RARa, PRAME, Proteinase-3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1.

DETAILED DESCRIPTION OF THE INVENTION

According to the invention, standard methods can be used for production of recombinant nucleic acids, cultivation of cells and introduction of nucleic acids into cells. Enzymatic reactions take place according to the manufacturer's instructions or in a manner known per se.

The term "Flt3 ligand" or "Flt3-L" refers to "Fms-like tyrosine kinase 3 ligand". Flt3 is a receptor tyrosine kinase (RTK), which is expressed by immature hematopoietic precursor cells. The ligand for Flt3 (Flt3-L) is a transmembrane protein or soluble protein and is expressed by a large number of cells, including hematopoietic cells and stroma cells in the bone marrow. In combination with other growth factors, the ligand stimulates proliferation and development of various cell types, including stem cells, myeloid and lymphoid precursor cells, dendritic cells and NK cells. Activation of the receptor leads to a tyrosine-phosphorylation of various key-adaptor proteins, which are known to be involved in various signal transduction pathways, which control proliferation, survival and other processes in hematopoietic cells.

The term "Flt3 ligand" comprises any molecules, in particular peptides and proteins, that bind to Flt3 receptors and preferably have the biological activity for transducing a stimulatory signal to the cell via the bound Flt3 receptor.

The term "Flt3 ligand" comprises all variants, in particular splice variants and posttranslationally modified variants, conformations, isoforms and species-homologs of Flt3 ligand, which are expressed naturally by cells or which are expressed by cells that have been transfected with a nucleic acid that codes for Flt3 ligand. Moreover, the term "Flt3 ligand" comprises all forms of Flt3 ligand that have been produced and can be produced by recombinant methods.

The term "nucleic acid that codes for Flt3 ligand" preferably refers to a nucleic acid that comprises a nucleic acid sequence that is selected from the group consisting of (i) SEQ ID NOs: 3 and 4 of the sequence listing, (ii) a sequence derived from the nucleic acid sequence according to (i), and (iii) a part of the nucleic acid sequence according to (i) or (ii).

In a preferred embodiment, Flt3 ligand comprises an amino acid sequence that is encoded by a nucleic acid that comprises a nucleic acid sequence that is selected from the group consisting of (i) SEQ ID NOs: 3 and 4 of the sequence listing, (ii) a sequence derived from the nucleic acid sequence according to (i), and (iii) a part of the nucleic acid sequence according to (i) or (ii). In another preferred embodiment, Flt3 ligand comprises an amino acid sequence that is selected from the group consisting of SEQ ID NOs: 1 and 2 of the sequence listing, a sequence derived therefrom, or a part thereof.

Forms of Flt3 ligand that can be used according to the invention comprise, but are not limited to, Flt3 ligand from mouse and humans as shown in SEQ ID NOs: 1 and 2 of the sequence listing and polypeptides with sequences derived therefrom.

With reference to SEQ ID NOs: 1 and 2, the term "sequence derived therefrom" preferably refers to sequences that are shortened relative to SEQ ID NOs: 1 and 2 and mainly comprise the extracellular portion of the proteins. Such sequences preferably do not comprise the transmembrane portion and intracellular portion. The term "Flt3 ligand" comprises polypeptides as described in U.S. Pat. No. 5,554,512 and in U.S. Pat. No. 6,291,661, which are included herein by reference.

Especially preferred forms of Flt3 ligand are biologically active, soluble forms and in particular those forms that comprise the extracellular domain or one or more fragments of the extracellular domain. Such forms preferably do not comprise the transmembrane portion and intracellular, i.e. cytoplasmic, portion of Flt3 ligand. Soluble forms of Flt3 ligand are polypeptides that can be secreted from the cells in which they are expressed. In said forms the intracellular domain and the transmembrane domain of the polypeptide or a part thereof are deleted, so that the polypeptide is secreted completely from the cell in which it is expressed. The intracellular domain and transmembrane domain of the polypeptides can be determined according to the invention in a manner that is known per se by known methods for determination of said domains on the basis of sequence information. With reference to SEQ ID NO: 1 the intracellular domain can be defined as amino acids 206-235 and the transmembrane domain as amino acids 185-205 or 183-205.

Human Flt3 ligand can comprise an amino acid sequence that is selected from the group consisting of amino acids 1-X, 27-X or 28-X of SEQ ID NO: 1 or a sequence derived therefrom, in which X represents an amino acid from 160-235, preferably 160, 161, 162, 163, 164, 165, 166, 167, 168, 169, 170, 171, 172, 173, 174, 175, 176, 177, 178, 179, 180, 181, 182, 183, 184, or 185.

Murine Flt3 ligand can comprise an amino acid sequence that is selected from the group consisting of amino acids 1-Y, 27-Y or 28-Y of SEQ ID NO: 2 or a sequence derived therefrom, in which Y represents an amino acid from 163-232.

Embodiments of soluble human Flt3 ligand comprise the amino acid sequence of residues 1-160 of SEQ ID NO: 1 (inclusive), 27-160 of SEQ ID NO: 1 (inclusive), 28-160 of SEQ ID NO: 1 (inclusive), 1-179 of SEQ ID NO: 1 (inclusive), 27-179 of SEQ ID NO: 1 (inclusive), 28-179 of SEQ ID NO: 1 (inclusive), 1-182 of SEQ ID NO: 1 (inclusive), 27-182 of SEQ ID NO: 1 (inclusive), 28-182 of SEQ ID NO: 1 (inclusive), 1-185 of SEQ ID NO: 1 (inclusive), 27-185 of SEQ ID NO: 1 (inclusive), 28-185 of SEQ ID NO: 1 (inclusive), 1-235 of SEQ ID NO: 1 (inclusive), 27-235 of SEQ ID NO: 1 (inclusive) and 28-235 of SEQ ID NO: 1 (inclusive).

Embodiments of soluble murine Flt3 ligand comprise the amino acid sequence of residues 1-163 of SEQ ID NO: 2 (inclusive), the amino acid sequence of residues 28-163 of SEQ ID NO: 2 (inclusive), the amino acid sequence of residues 1-188 of SEQ ID NO: 2 (inclusive), the amino acid sequence of residues 28-188 of SEQ ID NO: 2 (inclusive), the amino acid sequence of residues 1-232 of SEQ ID NO: 2 (inclusive) and the amino acid sequence of residues 28-232 of SEQ ID NO: 2 (inclusive).

The term "Flt3 ligand" also comprises, according to the invention, molecules that comprise the aforementioned sequences in combination, preferably in the form of a covalent fusion, with one or more heterologous peptides or proteins, optionally separated by a linker. In this connection, a peptide or protein is heterologous to a sequence with which it is combined, if the peptide or protein does not occur naturally in combination with the sequence. For example, sequences that are derived from a natural Flt3 ligand, and sequences that are derived from antibodies, are heterologous sequences. These heterologous peptides or proteins can for example control secretion of the aforementioned sequences from a host cell, bring about compartmentalization of the aforementioned sequences in particular organelles of a cell, increase the stability of the aforementioned sequences and/or make possible or facilitate purification. In one embodiment the heterologous peptide or protein is derived from an antibody, preferably the heavy chain of an antibody, in particular an antibody of class IgG1, IgG2, preferably IgG2a, IgG2b, IgG3, IgG4, IgM, IgA, preferably IgA1, IgA2, secretory IgA, IgD or IgE. Preferably the heterologous peptide or protein is derived from the constant region of an antibody and preferably comprises this region or a part thereof. Preferably the heterologous peptide or protein comprises the sequence shown in SEQ ID NO: 5 or a sequence derived therefrom. In one embodiment the Flt3 ligand according to the invention comprises the sequence shown in SEQ ID NO: 6 or a sequence derived therefrom.

Furthermore, the term "Flt3 ligand" according to the invention comprises all polypeptides that comprise an amino acid sequence that is derived from the sequences specifically described herein.

The term "immune response" is used herein in its conventional meaning and comprises humoral and cellular immunity. An immune response is manifested by the occurrence of one or more reactions, which are selected from development of antibodies to an antigen and expansion of antigen-specific T lymphocytes, preferably CD4+ T lymphocytes and CD8+ T lymphocytes, more preferably CD8+ T lymphocytes, which can be detected in various proliferation or cytokine production tests in vitro.

The term "immunotherapy" refers to a treatment based on activation of a specific immune response.

Terms such as "protect", "prophylactic" or "protective" mean herein the preventing and/or treating of the occurrence and/or increase of a tumor or pathogen in an organism. A prophylactic administration of a vaccine can protect the recipient against development of tumor growth or against infection by a pathogen. A therapeutic administration of a vaccine or immunotherapy can protect the recipient for example against spread or metastasis of existing tumors or effect reduction of the tumor mass of existing tumors.

Antigen-presenting cells or APCs as used herein are cells that have peptide fragments of protein antigens in association with MHC molecules on their cell surface. Some APCs can activate antigen-specific T cells. Examples of APCs comprise, but are not limited to, dendritic cells, macrophages, monocytes, B cells and the like.

The term "MHC/peptide-complex" refers to a noncovalent complex of the binding domain of an MHC class I or MHC class II molecule and an MHC class I or MHC class II binding peptide.

The term "MHC binding peptide" or "binding peptide" refers to a peptide that binds to an MHC class I and/or an MHC class II molecule. In the case of class I MHC/peptide complexes the binding peptides are typically 8-10 amino acids long, although longer or shorter peptides may be effective. In the case of class II MHC/peptide complexes the binding peptides are typically 10-25 amino acids long and in particular 13-18 amino acids long, although longer and shorter peptides may be effective.

The term "major histocompatibility complex" and the abbreviation "MHC" refer to a complex of genes that occurs in all vertebrates. MHC proteins or molecules function, in signalling between lymphocytes and antigen-presenting cells in normal immune responses, by binding peptides and presenting them for possible recognition by T cell receptors (TCR). MHC molecules bind peptides in an intracellular processing compartment and present these peptides on the surface of antigen-presenting cells to T cells. The human MHC region, also termed HLA, is located on chromosome 6 and comprises the class I region and the class II region.

The term "MHC class I" or "class I" refers to the major histocompatibility complex class I proteins or genes. Within the MHC class I region, in humans there are the HLA-A, HLA-B, HLA-C, HLA-E, HLA-F, CD1a, CD1b and CD1c subregions.

The $\alpha$ chains of class I are glycoproteins with a molecular weight of about 44 kDa. The polypeptide chain is slightly longer than 350 amino acid residues. It can be divided into three functional regions: an external, a transmembrane and a cytoplasmic region. The external region is 283 amino acid residues long and is divided into three domains, $\alpha 1$, $\alpha 2$ and $\alpha 3$. The domains and regions are usually encoded by separate exons of the class I gene. The transmembrane region traverses the lipid bilayer of the plasma membrane. It consists of 23 mostly hydrophobic amino acid residues, which are arranged in an $\alpha$-helix. The cytoplasmic region, i.e. the part facing the cytoplasm, which is contiguous with the transmembrane region, is typically 32 amino acid residues long and is capable of interacting with the elements of the cytoskeleton. The $\alpha$ chain interacts with $\beta 2$ microglobulin and thus forms $\alpha$-$\beta 2$ dimers on the cell surface.

The term "MHC class II" or "class II" refers to the major histocompatibility complex class II proteins or genes. Within the MHC class II region, in humans there are the DP, DQ and DR subregions for class II $\alpha$ chain and $\beta$ chain genes (i.e. DP$\alpha$, DP$\beta$, DQ$\alpha$, DQ$\beta$, DR$\alpha$ and DR$\beta$).

Class II molecules are heterodimers, which consist of one $\alpha$ and of one $\beta$ chain. Both chains are glycoproteins with a molecular weight of 31-34 kDa ($\alpha$) or 26-29 kDa ($\beta$). The total length of the $\alpha$ chains varies from 229 to 233 amino acid residues, and that of the $\beta$ chains from 225 to 238 residues. $\alpha$ and $\beta$ chains both consist of an external region, a linking peptide, a transmembrane region and a cytoplasmic tail. The external region consists of two domains, $\alpha 1$ and $\alpha 2$ or $\beta 1$ and $\beta 2$. The linking peptide in $\alpha$ and $\beta$ chains is 13 and 9 residues long, respectively. It joins the second domain to the transmembrane region, which both in $\alpha$ and in $\beta$ chains consists of 23 amino acid residues. The length of the cytoplasmic region, i.e. the part facing the cytoplasm, which is contiguous with the transmembrane region, varies from 3 to 16 residues in $\alpha$ chains and from 8 to 20 residues in $\beta$ chains.

The term "MHC binding domain" refers to the "MHC class I binding domain" and "MHC class II binding domain".

The term "MHC class I binding domain" refers to the region of an MHC class I molecule or an MHC class I chain that is necessary for binding to an antigenic peptide. An MHC class I binding domain is mainly formed by the $\alpha 1$ and $\alpha 2$ domains of the MHC class I $\alpha$ chain. Although the $\alpha 3$ domain of the $\alpha$ chain and $\beta 2$ microglobulin do not represent essential parts of the binding domain, they are presumably important for stabilization of the whole structure of the MHC class I molecule and therefore the term "MHC class I binding domain" preferably includes these regions. An MHC class I binding domain can also be defined essentially as the extracellular domain of an MHC class I molecule, which distinguishes it from the transmembrane and cytoplasmic regions.

The term "MHC class II binding domain" refers to the region of an MHC class II molecule or an MHC class II chain that is necessary for binding to an antigenic peptide. An MHC class II binding domain is mainly formed by the $\alpha 1$ and $\beta 1$ domains of the MHC class II $\alpha$ and $\beta$ chains. The $\alpha 2$ and $\beta 2$ domains of these proteins are presumably, however, also important for stabilization of the whole structure of the MHC binding groove and therefore the term "MHC class II binding domain" according to the invention preferably includes these regions. An MHC class II binding domain can also be defined essentially as the extracellular domain of an MHC class II molecule, which distinguishes it from the transmembrane and cytoplasmic domain.

According to the invention, the term "antigen" covers any molecule that comprises at least one epitope. According to the invention, an antigen is preferably a molecule which, optionally after processing, can elicit an immune response, which preferably is specific to the antigen. Any suitable antigen that is a candidate for an immune response, where the immune response can be both a humoral, and a cellular immune response, can be used according to the invention. In the embodiments according to the invention, the antigen or a processed form thereof will preferably be presented by a cell in connection with MHC molecules, so that an immune response to the antigen or the processed form thereof is elicited.

The term "antigen" comprises in particular proteins, peptides, nucleic acids, in particular RNA, and nucleotides. An antigen is preferably a product that has been derived from allergens, viruses, bacteria, fungi, parasites and other infectious agents and pathogens, or tumor antigens. An antigen can according to the invention correspond to a naturally occurring product, e.g. a viral protein, or it can be derived therefrom, in particular by changing the order and/or length of the sequence, adding or inserting additional sequences etc., in particular in order to increase the immunogenicity. The antigen used will, however, preferably produce an immune response, which is also directed against the natural product from which it was derived. The term "antigen" therefore also comprises, according to the invention, immunogenic parts or epitopes of whole proteins or whole peptides, which can be in the form of proteins, peptides, multimeric proteins or peptides, synthetic peptides and the like. The term "immunogenicity" refers to the relative effectiveness of an antigen for producing an immune response.

The term "antigen" also comprises derivativized antigens, i.e. secondary substances that only become antigenic—and sensitizing—through transformation (e.g. intermediate transformation in the molecule, or by completing with somatic protein).

In a preferred embodiment the antigen is a tumor antigen, i.e. a constituent of cancer cells, which can be derived from the cytoplasm, the cell surface and the cell nucleus, in particular those antigens forming, preferably multiplied, intracellularly or as surface antigens on tumor cells. Examples are the carcinoembryonic antigen, $\alpha 1$-fetoprotein, isoferritin and fetal sulfoglycoprotein, $\alpha 2$-H-ferroprotein and $\gamma$-fetoprotein and various virus tumor antigens. In another embodiment the antigen is a virus antigen such as viral ribonucleoproteins or coat proteins. In particular the antigen or peptides thereof should be presented by MHC molecules and thus be capable of the modulation, in particular activation of cells of the immune system, preferably $CD4^+$ and $CD8^+$ lymphocytes, in particular via modulation of the activity of a T cell receptor and therefore preferably induce the multiplication of T cells.

According to the invention, a tumor antigen preferably comprises any antigen that is characteristic, with respect to type and/or quantity, of a tumor or cancer, or tumor or cancer cells.

Flt3 ligand can also be used in connection with a treatment of allergies. The immunization protocols using Flt3 ligand, described herein, can be applied in the allergen-specific immunotherapy of allergies. Allergen-specific immunotherapy is defined as the administration of preferably increasing doses of an allergen vaccine to an organism with one or more allergies, in order to achieve a state in which the symptoms that are associated with a subsequent exposure to the causative allergen are alleviated. The efficacy of an allergen-specific immunotherapy using Flt3 ligand can be assessed by known standard methods such as by measurement of allergen-specific IgG and IgE antibodies from the patient.

Immunogens are antigens that induce an immune response in an organism.

The compositions to be used according to the invention are not limited with respect to the type and number of antigens that are encoded by the RNA molecules.

According to the invention, an individual RNA species with a defined sequence can be administered, but it is also possible for several different RNAs with different sequences to be administered. In one embodiment, according to the invention a pool of RNA molecules is administered. In the case when the RNA comprises, according to the invention, RNA molecules with different sequences, the coding sequences of these RNAs can be derived from identical or different antigens.

The term "pathogen" refers to pathogenic microorganisms and comprises viruses, bacteria, unicellular organisms and parasites. Human immunodeficiency virus (HIV), cytomegalovirus (CMV), herpesvirus (HSV), hepatitis A virus (HAV), HBV, HCV, papillomavirus and human T-lymphotropic virus (HTLV) are examples of pathogenic viruses. Unicellular organisms comprise plasmodia, trypanosomes, amoebas and the like.

The term "vaccine" as used herein refers to a composition that comprises one or more antigens or the nucleic acid(s) encoding them. A vaccine can furthermore comprise one or more adjuvants, diluents, excipients and the like and is administered to an organism by any suitable route, in order to produce a protective and/or therapeutic immune response to an antigen. A vaccine can therefore serve for preventing a disease and can for example be administered prior to infection or it can be administered after the onset of a disease. A vaccine can comprise natural, derivativized, synthetic, recombinant or non-recombinant antigens or the nucleic acid(s) encoding them. According to the invention, a vaccine contains RNA, which has polynucleotide sequences that code for one or more antigens. The RNA can be naked RNA or can be incorporated in liposomes or other particles for gene transfer. Other agents that can be incorporated in the vaccine in order to facilitate administration comprise polypeptides, peptides, polysaccharide conjugates, lipids and the like.

A person skilled in the art will know that one of the principles of immunobiology and vaccination is based on the fact that an immunoprotective reaction to a disease is produced by immunizing an organism with an antigen, which is immunologically relevant with respect to the disease to be treated. It will therefore be understood that in the methods according to the invention for treatment of cancer, infectious diseases and the like, vaccines should be included that comprise antigens that are immunologically relevant for the disease that is to be prevented or treated. For example, cancer vaccines would comprise one or more cancer antigens.

In the case of an RNA vaccine, an RNA, which codes operatively for an immunogenic peptide or protein and is preferably in a pharmaceutically compatible excipient, is administered to the cells of an animal, which for example has cancer or a pathogenic infection, wherein the RNA is incorporated into the cells and an amount of an immunogenic peptide or protein is produced, which, optionally after processing, is capable of producing a protective or therapeutically effective immune response.

The RNA material supplied to the cells can contain the complete sequence or only a part of an immunogenic peptide or protein. It can also contain sequences that code for other polypeptide sequences. Furthermore, it can contain elements that are involved in regulation of gene expression (e.g. promoter, enhancer, 5'- or 3'-UTR sequences, and the like). The RNA can also comprise an immunostimulating sequence, which intensifies the immunogenicity of a particular gene product and/or it can comprise sequences that enhance the uptake of the polynucleotide.

It should be noted in this connection that for efficacy, a vaccine according to the invention can only produce immunity in a part of the population, as some individuals might not have any capacity for producing a robust or protective immune response or in some cases for producing any immune response to the vaccine. This incapacity might have its cause in the individual's genetic background or in an immunodeficiency state (either acquired or congenital) or in immunosuppression (for example through treatment with immunosuppressants, to prevent organ rejection or to suppress an autoimmune state).

Effector cells as described herein are cells that perform effector functions during an immune response. These cells secrete for example cytokines and/or chemokines, kill microbes, recognize infected or degenerated cells and optionally kill them and secrete antibodies. Examples comprise, but are not limited to, T cells (cytotoxic T cells, helper T cells, tumor-infiltrating T cells), B cells, NK cells, neutrophils, macrophages and dendritic cells.

Dendritic cells comprise a heterogeneous cell population with particular morphology and a wide-ranging tissue distribution. The dendritic cell system and its role in the immune system were discussed by Steinman, R. M., Annu. Rev. Immunol., 9:271-296 (1991), said disclosure being included by reference. Dendritic cells possess a capacity for sensitization of MHC-restricted T cells and are very effective in presenting antigens against T cells. The term "dendritic cells" or "DCs" refers to members of a diverse population of morphologically similar cell types, which occur in lymphoid or nonlymphoid tissues. Dendritic cells are a class of "professional" antigen-presenting cells and have a capability for sensitization of MHC-restricted T cells. Depending on the particular line and the particular level of maturity, dendritic cells can be recognized by function or phenotype, in particular by the cell surface phenotype. These cells are characterized by a particular morphology, phagocytic/endocytic capability, a high degree of surface MHC class II expression and the capability of presenting antigens against T cells, in particular naive T cells. Functionally, dendritic cells can be identified by a test in which the capacity for antigen presentation is determined. Said test can comprise an assessment of the capacity for stimulating T cells through presentation of a test antigen, and optionally determination of T cell proliferation, release of IL-2 and the like.

According to the invention, lymphoid dendritic cells that have been exposed in vivo or in vitro to RNA can be used as antigen-presenting cells for the induction of an immune response to antigens that are encoded by the RNA.

Immunoadjuvants or adjuvants are compounds which, when administered to an individual, increase the immune response to an antigen relative to a test individual to whom only the antigen is administered, or intensify certain activities of cells of the immune system.

According to the invention, RNA coding for one or more antigens can be administered with any adjuvant. The term "adjuvant" then refers to any substance that is different from the antigen and Flt3 ligand, and when included in a vaccine accelerates, prolongs or intensifies the immune response of a host to an antigen. Although Flt3 ligand is not, according to the invention, regarded as an adjuvant as defined herein, it can nevertheless be regarded as an adjuvant on the basis of its described action of intensifying immune responses. However, for clarity, Flt3 ligand is not designated as an adjuvant here. It is thought that adjuvants exert their biological effects by one or more mechanisms, including an increase in surface area of an antigen, prolongation of retention of the antigen in the body, slowing of the release of the antigen, targeting an antigen on macrophages, increasing antigen uptake, increasing antigen processing, stimulation of cytokine release, stimulation and activation of immune cells such as B cells, macrophages, dendritic cells, T cells and some other kind of triggering of a nonspecific activation of the cells of the immune system. Adjuvants comprise a heterogeneous group of compounds such as oil emulsions (for example Freund's adjuvant), mineral compounds (such as alum), bacterial products (such as *Bordetella pertussis* toxin), liposomes and immunostimulating complexes.

An "auxiliary molecule" as defined herein is a molecule that optionally is administered to an organism, to accelerate, prolong or intensify the immune response of the organism to an antigen. For example, cytokines, growth factors and the like can be used in enhancing or modulating an immune response. Cytokines comprise, but are not limited to, interleukins such as interleukin-1, 2, 3, 4, 5, 6, 7, 10, 12, 15, 18 and 23, chemokines, GM-CSF, G-CSF, interferon-α and -γ, members of the TNF family such as TNF-α, TGF-β, CpG sequences and the like.

The RNA supplied to the cells can also be antisense-RNA or siRNA. Therefore the Flt3 ligand described according to the invention herein can be used for supplying antisense-RNA or siRNA into target cells.

A composition's ability to modulate the activity of T cell receptors can easily be determined by an in-vitro test. Typically, T cells for the tests are supplied by transformed T cell lines, such as T cell hybridomas or T cells that are isolated from a mammal such as a human or a rodent such as a mouse. Suitable T cell hybridomas are readily available or can be produced in a manner known per se. T cells can be isolated from a mammal in a manner known per se; cf. e.g. Shimonkevitz, R. et al., 1983, J. Exp. Med. 158:303.

A suitable test for determining whether a composition is capable of modulating activity of T cells is carried out as follows by the following steps 1-4. T cells express a marker in a suitable way, which can be tested and which indicates T cell activation or modulation of T cell activity after activation. Thus, it is possible to use the mouse T cell hybridoma DO11.10, which expresses interleukin-2 (IL-2) on activation. IL-2 concentrations can be measured, to determine whether a composition is capable of modulating the activity of this T cell hybridoma. A suitable test of this kind takes place by the following steps:

1. T cells are obtained e.g. from a T cell hybridoma of interest or by isolation from a mammal.
2. The T cells are cultivated under conditions that permit multiplication.
3. The growing T cells are brought in contact with antigen-presenting cells, which in their turn had been brought in contact with an antigen or a nucleic acid coding therefor.
4. The T cells are tested for a marker, e.g. the IL-2 production is measured.

The T cells used in the tests are incubated in conditions suitable for multiplication. For example, a DO11.10 T cell hybridoma is suitably incubated at about 37° C. and 5% $CO_2$ in the complete medium (RPMI 1640, supplemented with 10% FBS, penicillin/streptomycin, L-glutamine and $5 \times 10^{-5}$ M 2-mercaptoethanol). T cell activation signals are provided by antigen-presenting cells, which had been loaded with the appropriate antigenic peptide.

As an alternative to the measurement of an expressed protein such as IL-2, the modulation of T cell activation can be suitably determined from changes in the multiplication of antigen-dependent T cells, as measured by known radiolabeling techniques. For example, a labeled (such as tritiated) nucleotide can be included in a test culture medium. The incorporation of this labeled nucleotide in the DNA serves as a measure of T cell multiplication. This test is not suitable for T cells that do not require antigen presentation for growth, such as T cell hybridomas. The test is suitable for measuring the modulation of T cell activation in the case of nontransformed T cells that were isolated from mammals.

The capacity for inducing an immune response, including for making vaccination against a target disease possible, can easily be determined by an in-vivo test. For example, a composition can be administered to a mammal such as a mouse and blood samples can be taken from the mammal at the timepoint of the first administration and repeatedly at regular intervals thereafter (such as 1, 2, 5 and 8 weeks after administration). Serum is obtained from the blood samples and is assayed for the development of antibodies resulting from the immunization. Antibody concentrations can be determined. In addition, T lymphocytes can be isolated from the blood or from lymphatic organs and tested functionally for reactivity to the antigen or epitopes derived from the antigen. All "readout" systems known by a person skilled in the art, including proliferation assay, cytokine secretion, cytotoxic activity, and tetramer analysis can be used for this.

A nucleic acid molecule or a nucleic acid sequence relates according to the invention to a nucleic acid, which preferably is deoxyribonucleic acid (DNA) or ribonucleic acid (RNA). Nucleic acids comprise, according to the invention, genomic DNA, cDNA, mRNA, molecules produced by recombinant techniques and those chemically synthesized. A nucleic acid can, according to the invention, be in the form of a single-stranded or double-stranded and linear or covalently circularly closed molecule.

The term "RNA" refers to a molecule that comprises at least one ribonucleotide residue. "Ribonucleotide" refers to a nucleotide with a hydroxyl group in the 2'-position of a beta-D-ribofuranose group. The term comprises double-stranded RNA, single-stranded RNA, isolated RNA, such as partially or completely purified RNA, substantially pure RNA, synthetic RNA, recombinantly produced RNA, and altered RNA, which differs from the naturally occurring RNA through the addition, deletion, substitution and/or alteration of one or more nucleotides. These changes can comprise the addition of non-nucleotide material, such as on the end(s) of an RNA or within it, for example on one or more nucleotides of the RNA. Nucleotides in RNA molecules can also comprise nonstandard nucleotides such as nucleotides that do not occur naturally or chemically synthesized nucleotides or deoxynucleotides. These altered RNAs can be designated as analogs or as analogs of naturally occurring RNA.

"mRNA" denotes "messenger-RNA" and refers to a "transcript", which is produced using DNA as template and itself codes for a peptide or protein. An mRNA typically comprises a 5'-untranslated region, a protein-coding region and a 3'-untranslated region. mRNA has a limited half-life in cells and in vitro. According to the invention, mRNA can be produced by in-vitro transcription of a DNA template.

According to the invention, RNA can be provided with modifications, which for example increase the stability of the RNA and/or the efficiency with which the RNA is translated. Thus, the RNA can for example be provided with a poly(A) sequence, in particular an open-ended poly(A) sequence. It has been shown that RNA with an open-ended poly(A) sequence is translated more efficiently than RNA with a poly(A) sequence with a concealed end. Moreover, it was found that a long poly(A) sequence, in particular of about 120 bp, leads to an optimal transcript stability and translation efficiency of RNA. It was also shown that a doubled 3'-untranslated region (UTR), in particular of the human beta-globin gene, in an RNA molecule leads to an improvement of translation efficiency, far above the summation effect to be expected with two individual UTRs. A combination of the modifications described above can have a synergistic influence on stabilization of the RNA and increase of translation. Such modifications are described in PCT/EP2006/009448, which is included herein by reference, and are envisaged according to the invention.

Preferably, according to the invention, a modification and consequent stabilization and/or increase in translation efficiency of RNA is achieved by genetic-engineering modification of the expression vectors, which preferably serve as template for the in-vitro transcription of RNA.

Said vectors should in particular permit the transcription of RNA with a poly(A) sequence, wherein the poly(A) sequence preferably has an open end in the RNA, i.e. no nucleotides different from A nucleotides flank the poly(A) sequence at its 3'-end. An open-ended poly(A) sequence in the RNA can be achieved by introducing a restriction cleavage site of type IIs into an expression vector, which permits the transcription of RNA under the control of a 5' located RNA-polymerase promoter and contains a polyadenylation cassette (poly(A) sequence), wherein the recognition sequence is positioned 3' from the poly(A) sequence, whereas the cleavage site is located upstream and thus within the poly(A) sequence. By restriction cleavage on the restriction cleavage site of type IIs, in a plasmid a linearization of the plasmid becomes possible within the poly(A) sequence. The linearized plasmid can then be used as a template for an in-vitro transcription, wherein the resultant transcript ends in an unconcealed poly(A) sequence.

Furthermore or alternatively, according to the invention a modification and hence stabilization and/or increase of the translation efficiency of RNA can be achieved by genetically engineering expression vectors so that they allow the transcription of RNA with two or more 3'-untranslated regions on their 3'-end and preferably between the sequence coding for a peptide or protein (open reading frame) and the poly(A) sequence.

In a preferred embodiment, RNA according to the invention is obtained by in-vitro transcription of a suitable DNA template. The promoter for controlling the transcription can be any promoter for an RNA-polymerase. Specific examples of RNA-polymerases are the T7, T3 and SP6 RNA-polymerases. The in-vitro transcription is preferably controlled according to the invention by a T7 or SP6 promoter.

A DNA template for in-vitro transcription can be produced by cloning a nucleic acid, in particular cDNA, and inserting the nucleic acid into a vector suitable for in-vitro transcription.

According to the invention, the term "RNA that encodes" means, with respect to an antigen, that the RNA, if it is in a suitable environment, preferably in a cell, can be expressed, in order to produce the antigen. Preferably the RNA is capable of interacting with the cellular translation machinery, to provide the antigen that it encodes.

If there is a reference, according to the invention, that RNA expresses more than one antigen, the RNA can comprise various RNA molecules, which express various of these several antigens. However, the invention also comprises cases in which an RNA molecule expresses various antigens, which optionally are joined together.

According to the invention, any technology that is suitable for transferring RNA into cells can be used in order to introduce RNA into cells. Preferably RNA is transfected into cells by standard techniques. Said techniques comprise electroporation, lipofection and microinjection. Preferably introduction of RNA, which codes for an antigen, into a cell causes expression of antigen in the cell.

Furthermore, the term "nucleic acid" also comprises derivatives of nucleic acids or nucleic acid sequences such as a chemical derivatization of a nucleic acid on a nucleotide base, on the sugar or on the phosphate and nucleic acids that contain nucleotides and nucleotide analogs that do not occur naturally.

"3'-end of a nucleic acid" refers according to the invention to that end on which there is a free hydroxyl group. In the schematic representation of double-stranded nucleic acids, in particular DNA, the 3'-end is always located on the right. "5'-end of a nucleic acid" refers according to the invention to that end on which a free phosphate group is located. In the schematic representation of double-stranded nucleic acids, in particular DNA, the 5'-end is always located on the left.

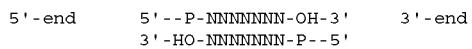

"Functional coupling" or "functionally coupled" refers according to the invention to coupling in a functional relationship. A nucleic acid is "functionally coupled" if it is placed in a functional relationship with another nucleic acid sequence. For example, a promoter is functionally coupled to a coding sequence if it influences the transcription of the coding sequence. Functionally coupled nucleic acids are typically adjacent to one another, optionally separated by additional nucleic acid sequences.

The nucleic acids described according to the invention are preferably isolated. The term "isolated nucleic acid" means, according to the invention, that the nucleic acid (i) was amplified in vitro, for example by polymerase chain reaction (PCR), (ii) was produced recombinantly by cloning, (iii) was purified, for example by cleavage and separation by gel electrophoresis, or (iv) was synthesized, for example by chemical synthesis. An isolated nucleic acid is a nucleic acid that is available for manipulation by recombinant DNA techniques.

According to the invention, a "nucleic acid sequence that has been derived from a nucleic acid sequence" refers to a nucleic acid in which, in comparison with the nucleic acid from which it was derived, there are individual or multiple nucleotide substitutions, deletions and/or additions, wherein there is a certain degree of homology between the nucleic acids, i.e. the nucleic acids have significant direct or complementary agreements in the sequence of their nucleotides. A nucleic acid derived from a nucleic acid has, according to the invention, a functional property of the nucleic acid from which it was derived. Such properties are defined in particular by the properties of the expression products of the nucleic acids. In the case of Flt3 ligand this relates in particular to the properties of binding to Flt3 receptor and preferably having the biological activity for transducing a stimulatory signal to the cell via the bound Flt3 receptor, and/or when administered concomitantly with a vaccine-RNA, to be able to intensify the immune response elicited by the RNA. In the case of antigens this relates to the property of being able to elicit an immune response with comparable specificity and/or reactivity. An example of a "nucleic acid sequence that has been derived from a nucleic acid sequence" is a nucleic acid in which, in comparison with the nucleic acid from which it was derived, there are codon optimizations, for example for better expression in a particular host organism or a particular host cell.

A sequence derived from a nucleic acid sequence or the term "sequence derived from a nucleic acid sequence" refers preferably to homologous sequences.

Preferably the degree of identity between homologous nucleic acids according to the invention is at least 70%, in particular at least 75%, at least 80%, at least 85%, at least 90%, at least 95%, at least 96%, at least 97%, at least 98%, and preferably at least 99%. The degree of identity is preferably stated for a region of at least about 30, at least about 50, at least about 70, at least about 90, at least about 100, at least about 150, at least about 200, at least about 300, at least about 400, at least about 500, or at least about 1000 consecutive nucleotides. In preferred embodiments, the degree of identity is stated for the total length of the reference nucleic acid such as the nucleic acid sequences given in the sequence listing.

The term "percentage identity" denotes a percentage of nucleotides, which are identical between two sequences to be compared when there is optimal alignment, wherein said percentage is purely statistical, the differences between the two sequences can be distributed randomly and over the whole sequence length and the sequence to be compared can comprise additions or deletions in comparison with the reference sequence, in order to achieve optimal alignment between two sequences. Sequence comparisons between two sequences are generally carried out by comparing these sequences after optimal alignment relative to a segment or "comparison window", to identify local regions of sequence agreement. Optimal alignment for purposes of comparison can be performed manually or by means of the local homology algorithm of Smith and Waterman, 1981, Ads App. Math. 2, 482, by means of the local homology algorithm of Neddleman and Wunsch, 1970, J. Mol. Biol. 48, 443, and by means of the similarity search algorithm of Pearson and Lipman, 1988, Proc. Natl. Acad. Sci. USA 85, 2444, or with the aid of computer programs that use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is obtained by determining the number of identical positions at which the sequences to be compared agree, dividing this number by the positions compared and multiplying this result by 100.

For example, it is possible to use the BLAST program "BLAST 2 sequences", which is obtainable from the website of the National Center for Biotechnology Information (NCBI).

A nucleic acid is in particular "homologous" to another nucleic acid when the two sequences of the complementary strands hybridize to one another and can enter into a stable duplex, wherein the hybridization preferably takes place under conditions that allow a specific hybridization between polynucleotides (stringent conditions). Stringent conditions are described for example in Molecular Cloning: A Laboratory Manual, J. Sambrook et al., Ed., 2nd edition, Cold Spring Harbor Laboratory Press, Cold Spring Harbor, N.Y., 1989 or Current Protocols in Molecular Biology, F. M. Ausubel et al., Ed., John Wiley & Sons, Inc., New York, and relate for example to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane onto which the DNA was transferred is washed for example in 2×SSC at room temperature and then in 0.1-0.5×SSC/0.1×SDS at temperatures up to 68° C.

Percentage complementarity states the percentage of consecutive nucleotides in a nucleic acid that can form hydrogen bonds with a second nucleic acid (e.g. by Watson-Crick base pairing). Complementary nucleic acids preferably have, according to the invention, at least 40%, in particular at least 50%, at least 60%, at least 70%, at least 80%, at least 90% and preferably at least 95%, at least 98% or at least 99% complementary nucleotides. Preferably, complementary nucleic acids are completely complementary, which means that all consecutive nucleotides will form hydrogen bonds with the same number of consecutive nucleotides in a second nucleic acid.

"Sequence similarity" shows the percentage of amino acids that are either identical or represent conservative amino acid substitutions. "Sequence identity" between two polypeptides or nucleic acids gives the percentage of amino acids or nucleotides that are identical between the sequences.

"Derivative" of a nucleic acid means, according to the invention, that there are individual or multiple nucleotide substitutions, deletions and/or additions in the nucleic acid. Furthermore, the term "derivative" also comprises a chemical derivatization of a nucleic acid on a base, a sugar or phosphate of a nucleotide. The term "derivative" also comprises nucleic acids that contain nucleotides and nucleotide analogs that are not naturally occurring.

Derivatives of a particular nucleic acid refer in particular to variants of the nucleic acid, in particular splice variants, isoforms and species homologs of the nucleic acid, in particular those that are expressed naturally.

Nucleic acids can be analyzed according to the invention with respect to variants such as splice variants in a manner known per se. Techniques for analysis of splice variants comprise reverse-transcription polymerase chain reaction (RT-PCR), Northern blotting and in-situ hybridization.

A technique called "RNAse protection" can also be used, in order to identify alternatively spliced mRNAs. RNAse protection comprises the transcription of a gene sequence to synthetic RNA, which is hybridized to RNA, which for example was derived from other cells. The hybridized RNA is then incubated with enzymes that recognize RNA:RNA hybrid mispairings. Fragments that are smaller than expected indicate the presence of alternatively spliced mRNAs. The putative alternatively spliced mRNAs can be cloned and sequenced in a manner known per se.

RT-PCR can also be used for identifying alternatively spliced mRNAs. In RT-PCR, mRNA is converted to cDNA by the enzyme reverse transcriptase in a manner known per se. The whole coding sequence of the cDNA is then amplified by means of PCR using a forward primer, located in the 3'-untranslated region, and a reverse primer, located in the 5'-untranslated region. The amplification products can be analyzed, for example by means of agarose-gel electrophoresis, with respect to alternative splice forms, for example by comparing the size of the amplified products with the size of the expected product from normally spliced mRNA. Any changes with respect to the size of the amplification products may indicate alternative splicing.

mRNA derived from mutated genes can also be identified simply by means of the techniques described above for the identification of alternative splice forms. For example, allelic forms of genes and the mRNA produced by them, which according to the invention are regarded as "mutants", can be identified.

Nucleic acids can, according to the invention, be present alone or in combination with other nucleic acids, which can be homo- or heterologous. In particular embodiments a nucleic acid according to the invention is functionally coupled to expression control sequences, which can be homologous or heterologous with respect to the nucleic acid. The term "homologous" denotes that a nucleic acid is also coupled functionally naturally to the nucleic acid with which it is combined, and the term "heterologous" denotes that a nucleic acid is not naturally coupled functionally to the nucleic acid with which it is combined.

A transcribable nucleic acid, in particular a nucleic acid coding for a peptide or protein, and an expression control sequence are coupled to one another "functionally" if they are linked together covalently in such a way that the transcription or expression of the transcribable and in particular coding nucleic acid is under the control or under the influence of the expression control sequence. If the nucleic acid is to be translated to a functional peptide or protein, in a functional coupling of an expression control sequence to the coding sequence, an induction of the expression control sequence leads to a transcription of the coding sequence, without resulting in a reading frame shift in the coding sequence or to an inability of the coding sequence to be translated to the desired peptide or protein.

According to the invention, the term "expression control sequence" comprises promoters, ribosome-binding sequences and other control elements, which control the transcription of a gene or the translation of the derived RNA. In particular embodiments according to the invention, the expression control sequences can be regulated. The precise structure of the expression control sequences can vary depending on the species or depending on the cell type, but generally comprises 5'-untranscribed and 5'- and 3'-untranslated sequences that are involved in the initiation of transcription or translation such as TATA-Box, Capping Sequence, CAAT Sequence and the like. In particular, 5'-untranscribed expression control sequences comprise a promoter region, which includes a promoter sequence for a transcriptional control of the functionally coupled gene. Expression control sequences can also comprise enhancer sequences or upstream activator sequences.

The term "promoter" or "promoter region" refers to a DNA sequence that is located upstream (5') to the coding sequence of a gene and controls the expression of the coding sequence by providing a recognition and binding site for RNA-polymerase. The promoter region can contain further recognition or binding sites for other factors that are involved in regulation of transcription of the gene. A promoter can control the transcription of a prokaryotic or eukaryotic gene. A promoter can be "inducible" and initiate transcription in response to an inducing agent or it can be "constitutive", if the transcription is not controlled by an inducing agent. An inducible promoter is not expressed or is only expressed to a very slight extent, in the absence of the inducing agent. In the presence of the inducing agent the gene is "switched on" or the transcription level is increased. This is brought about conventionally by the binding of a specific transcription factor.

Promoters preferred according to the invention are for example promoters for SP6-, T3- or T7-polymerase.

The term "expression" is used according to the invention in its broadest sense and comprises the production of RNA, or of RNA and protein. It also comprises a partial expression of nucleic acids. With reference to RNA, the term "expression" or "translation" refers in particular to the production of peptides or proteins. Expression can take place in a transient or stable manner.

A nucleic acid that codes for a protein or peptide can according to the invention be coupled to another nucleic acid that codes for a peptide sequence, which for example controls secretion of the protein or peptide encoded by the nucleic acid from a host cell or increases the immunogenicity of the protein or peptide encoded by the nucleic acid. A nucleic acid can according to the invention also be coupled to another nucleic acid that codes for a peptide sequence which brings about the anchoring of the encoded protein or peptide on the cell membrane of a host cell or its compartmentalization in particular organelles of this cell. Equally, there may be coupling to a nucleic acid that represents a reporter gene or any "tag".

The term "transcription" refers according to the invention to a process in which the genetic code in a DNA sequence is transcribed to RNA. After that, the RNA can be translated to protein. According to the invention, the term "transcription" comprises "in-vitro transcription", with the term "in-vitro transcription" referring to a method in which RNA, in particular mRNA, is synthesized in vitro cell-free, i.e. preferably using suitably prepared cellular extracts. Cloning vectors, which are generally called transcription vectors and according to the invention are covered by the term "vector", are preferably used for the production of transcripts.

The term "translation" refers according to the invention to a process in the ribosomes, by which a strand of mRNA controls the assembly of an amino acid sequence, to produce a protein or peptide.

The 3'-untranslated region refers to a region, located at the 3'-end of a gene downstream from the stop codon of a protein-coding region, which is transcribed, but is not translated to an amino acid sequence.

According to the invention, a first polynucleotide region is considered to be located downstream to a second polynucleotide region if the 5'-end of the first polynucleotide region is the nearest part of the first polynucleotide region to the 3'-end of the second polynucleotide region.

The 3'-untranslated region typically extends from the stop codon for a translation product to the poly(A) sequence, which conventionally is added on after the transcription process. The 3'-untranslated regions of mammalian mRNA typically have a homology region which is known as the AAUAAA hexanucleotide sequence. This sequence is presumably the poly(A) addition signal. Often it is 10 to 30 bases before the poly(A) addition site.

3'-Untranslated regions can contain one or more inverted repetitions, which can fold into stem-loop structures, which function as a barrier to exoribonucleases or interact with proteins that are known to increase RNA stability (e.g. RNA-binding proteins).

5'- and/or 3'-untranslated regions can according to the invention be coupled functionally to a transcribable and in particular coding nucleic acid, so that these regions are in a relationship with the nucleic acid in such a way that they increase the stability and/or translation efficiency of the RNA transcribed by the transcribable nucleic acid.

The 3'-untranslated regions of immunoglobulin-mRNAs are relatively short (less than about 300 nucleotides), whereas the 3'-untranslated regions of other genes are relatively long. For example, the 3'-untranslated region of tPA is about 800 nucleotides long, that of factor VIII is about 1800 nucleotides long and that of erythropoietin is about 560 nucleotides long.

According to the invention it can be determined whether a 3'-untranslated region or a nucleic acid sequence derived therefrom increases the stability and/or translation efficiency of RNA, by inserting the 3'-untranslated region or the nucleic acid sequence derived therefrom in the 3'-untranslated region of a gene and measuring whether this insertion increases the amount of the synthesized protein.

The foregoing applies appropriately to the case when according to the invention a nucleic acid comprises 2 or more 3'-untranslated regions, which are preferably coupled sequentially with or without a linker in-between, preferably in a "head-to-tail relationship" (i.e. the 3'-untranslated regions have the same orientation, preferably the orientation occurring naturally in a nucleic acid).

The term "gene" refers according to the invention to a particular nucleic acid sequence, which is responsible for the production of one or more cellular products and/or for the achievement of one or more intercellular or intracellular functions. In particular the term refers to a DNA segment that comprises a nucleic acid that codes for a specific protein or a functional or structural RNA molecule.

The terms "polyadenylation cassette" or "poly(A) sequence" refer to a sequence of adenyl residues that is typically located at the 3'-end of an RNA molecule. It is envisaged according to the invention that said sequence is added by a DNA template on the basis of repeating thymidyl residues in the strand complementary to the coding strand during transcription of RNA, whereas normally it is not coded in the DNA, but is attached to the free 3'-end of the RNA by a template-independent RNA-polymerase after transcription in the cell nucleus. According to the invention, a nucleotide sequence of at least 20, preferably at least 40, preferably at least 80, preferably at least 100 and preferably up to 500, preferably up to 400, preferably up to 300, preferably up to 200 and in particular up to 150 successive A nucleotides, and in particular about 120 successive A nucleotides is to be understood as a poly(A) sequence of this kind, where the term "A nucleotide" denotes adenyl residues.

"Restriction endonuclease" or "restriction enzyme" designates a class of enzymes that cleave phosphodiester bonds in both strands of a DNA molecule within specific base sequences. They recognize, on a double-stranded DNA molecule, specific binding sites, which are called recognition sequences. The places where the phosphodiester bonds in the DNA are cleaved by the enzymes are known as cleavage sites. In the case of type IIs enzymes, the cleavage site is at a defined distance from the DNA binding site. The term "restriction endonuclease" according to the invention comprises for example the enzymes SapI, EciI, BpiI, AarI, AloI, BaeI, BbvCI, PpiI and PsrI, BsrD1, BtsI, EarI, BmrI, BsaI, BsmBI, FauI, BbsI, BciVI, BfuAI, BspMI, BseRI, EciI, BtgZI, BpuEI, BsgI, MmeI, CspCI, BaeI, BsaMI, Mva1269I, PctI, Bse3DI, BseMI, Bst6I, Eam1104I, Ksp632I, BfiI, Bso31I, BspTNI, Eco31I, Esp3I, BfuI, Acc36I, AarI, Eco57I, Eco57MI, GsuI, AloI, Hin4I, PpiI, and PsrI.

"Half-life" refers to the length of time that is required for removal of half of the activity, amount or number of molecules.

In a preferred embodiment a nucleic acid molecule according to the invention is a vector. The term "vector" is used in its broadest sense and comprises any intermediate vehicles for a nucleic acid, which for example make it possible to introduce the nucleic acid into prokaryotic and/or into eukaryotic host cells and optionally integrate it into a genome. Said vectors are preferably replicated and/or expressed in the cell. Vectors comprise plasmids, phagemids or viral genomes. The term "plasmid", as used herein, generally refers to a construct of extrachromosomal genetic material, usually a circular DNA duplex, which can replicate independently of chromosomal DNA.

The term "host cell" refers according to the invention to any cell that is transformable or transfectable with an exogenous nucleic acid, preferably DNA or RNA. The term "host cell" comprises, according to the invention, prokaryotic cells (e.g. *E. coli*) or eukaryotic cells (e.g. mammalian cells, in particular human cells, yeast cells and insect cells). Mammalian cells such as cells from humans, mouse, hamster, pig, goat and primates are especially preferred. The cells can be derived from a large number of tissue types and can comprise primary cells and cell lines. Specific examples include keratinocytes, peripheral blood leukocytes, bone marrow stem cells and embryonic stem cells. In further embodiments the host cell is an antigen-presenting cell, where the term "antigen-presenting cell" comprises according to the invention dendritic cells, monocytes and macrophages. A nucleic acid can be present in the host cell in just one or in several copies and in one embodiment it is expressed in the host cell.

The term "peptide" refers to substances that comprise two or more, preferably 3 or more, preferably 4 or more, preferably 6 or more, preferably 8 or more, preferably 10 or more, preferably 13 or more, preferably 16 or more, preferably 20 or more and up to preferably 50, preferably 100 or preferably 150 successive amino acids, which are joined together by peptide bonds. The term "protein" or "polypeptide" refers to large peptides, preferably peptides with at least 151 amino acids, however, the terms "peptide", "polypeptide" and "protein" are generally used as synonyms herein. The terms "peptide", "polypeptide" and "protein" comprise, according to the invention, substances that contain not only amino acid constituents, but also non-amino acid constituents such as sugars and phosphate structures and also comprise substances that contain bonds such as ester, thioether or disulfide bonds.

A sequence derived from an amino acid sequence or the term "sequence derived from an amino acid sequence" refers according to the invention to homologous sequences and derivatives of the former sequence.

A sequence derived from an amino acid sequence has according to the invention a functional property of the amino acid sequence from which it is derived. In the case of Flt3 ligand this refers in particular to the properties of binding to Flt3 receptor and preferably to have the biological activity for transducing a stimulatory signal to the cell via the bound Flt3 receptor, and/or when administered concomitantly with a vaccine-RNA to be able to intensify the immune response elicited by the RNA. In the case of antigens this refers to the property of being able to elicit an immune response with comparable specificity and/or reactivity.

"Homologs" or "derivatives" of a protein or polypeptide or of an amino acid sequence in the sense of this invention comprise amino acid insertion variants, amino acid deletion variants and/or amino acid substitution variants.

Amino acid insertion variants comprise amino- and/or carboxy-terminal fusions, and insertions of single or several amino acids in a particular amino acid sequence. In the case of amino acid sequence variants with an insertion, one or more amino acid residues are inserted at a predetermined point in an amino acid sequence, although random insertion with suitable screening of the resultant product is also possible Amino acid deletion variants are characterized by the removal of one or more amino acids from the sequence. Amino acid substitution variants are characterized in that at least one residue in the sequence is removed and another residue is inserted in its place. Preferably the modifications are located in positions in the amino acid sequence that are not conserved between homologous proteins or polypeptides. Amino acids are preferably replaced with others with similar properties, such as hydrophobicity, hydrophilicity, electronegativity, volume of the side chain etc. (conservative substitution). Conservative substitutions refer for example to the replacement of one amino acid with another, both amino acids being listed in the same group given below:

1. Small aliphatic, nonpolar or slightly-polar residues: Ala, Ser, Thr (Pro, Gly)
2. Negatively charged residues and their amides: Asn, Asp, Glu, Gln
3. Positively charged residues: His, Arg, Lys
4. Large aliphatic, nonpolar residues: Met, Leu, Ile, Val (Cys)
5. Large aromatic residues: Phe, Tyr, Trp.

Three residues are put in parentheses owing to their special role for protein architecture. Gly is the only residue without a side chain and therefore endows the chain with flexibility. Pro has an unusual geometry, which limits the chain considerably. Cys can form a disulfide bridge.

The amino acid variants described above can easily be produced by known peptide synthesis techniques, e.g. by "solid phase synthesis" (Merrifield, 1964) and similar methods or by recombinant DNA manipulation. Techniques for inserting substitution mutations at predetermined points in DNA that possesses a known or partially known sequence are well known and comprise e.g. M13-mutagenesis. The manipulation of DNA sequences for producing proteins with substitutions, insertions or deletions and the general recombinant methods of expression of proteins e.g. in a biological system (such as mammalian, insect, plant and viral systems) are described in detail e.g. in Sambrook et al. (1989).

"Derivatives" of proteins or polypeptides also comprise according to the invention individual or multiple substitutions, deletions and/or additions of any molecules that are associated with the protein or polypeptide, such as carbohydrates, lipids and/or proteins or polypeptides.

In one embodiment, "derivatives" of proteins or polypeptides comprise those modified analogs that are formed by glycosylation, acetylation, phosphorylation, amidation, palmitoylation, myristoylation, isoprenylation, lipidation, alkylation, derivatization, insertion of protective/blocking groups, proteolytic cleavage or binding to an antibody or to another cellular ligand. Derivatives of proteins or polypeptides can also be produced by other methods, for example by chemical cleavage with cyanogen bromide, trypsin, chymotrypsin, papain, V8-protease, $NaBH_2$, acetylation, formylation, oxidation, reduction or by metabolic synthesis in the presence of tunicamycin.

Moreover, the term "derivative" also extends to all functional chemical equivalents of the proteins or polypeptides.

Derivatives of a particular protein or peptide also refer to post-translationally modified variants, isoforms and species-homologs of the protein or peptide, in particular those that are expressed naturally.

The proteins and peptides described according to the invention are preferably isolated. The terms "isolated protein" or "isolated peptide" mean that the protein or peptide has been isolated from its natural environment. An isolated protein or peptide may be in a substantially purified state. The term "substantially purified" means that the protein or peptide is essentially free from other substances, with which it is associated in nature or in vivo.

Proteins and peptides described according to the invention can be isolated from biological samples such as tissue or cell homogenates or can be expressed in a large number of eukaryotic and prokaryotic expression systems.

Preferably the degree of similarity, preferably identity between an amino acid sequence that is described herein, and an amino acid sequence that is derived from this amino acid sequence, is at least 70%, preferably at least 80%, still more preferably at least 90% or most preferably at least 95%, 96%, 97%, 98% or 99%. The degree of similarity or identity is preferably stated for a region of at least about 10, at least about 20, at least about 40, at least about 60, at least about 80, at least about 100, at least about 150, at least about 200, at least about 250, or at least about 300 consecutive amino acids. In preferred embodiments, the degree of identity is stated for the total length of the reference amino acid sequence.

With respect to identity of amino acid sequences, the above statements with respect to the identity of nucleic acid sequences apply appropriately.

A part, i.e. fragment, or derivative of a protein or peptide preferably has, according to the invention, a functional property of the protein or peptide from which it is derived. These functional properties are explained above for Flt3 ligand and antigens and comprise for example immune reactivity, in particular interaction with antibodies or interaction with other peptides or proteins. An important property is the capability of forming a complex with MHC molecules or Flt3-receptors and optionally producing or inhibiting an immune response for example by stimulation or inhibition of cytotoxic or helper T cells or triggering a cellular reaction. A part of a protein or peptide preferably comprises a sequence of at least 6, at least 8, at least 10, at least 12, at least 15, at least 20, at least 30 and preferably up to 8, up to 10, up to 12, up to 15, up to 20, up to 30 or up to 50 successive amino acids from the protein or peptide. In one embodiment a part of a protein or peptide refers according to the invention to one or more epitopes from the complete peptide or protein, wherein the several epitopes can be in their natural coupling or can have an artificial, i.e. not naturally occurring coupling, i.e. the epitopes can for example be separated from one another by an artificial linker. Preferably a part of a protein or peptide refers according to the invention to a sequence that is a target, in particular an epitope, for an immune response in a patient. In preferred embodiments the sequence is a target for an antibody- and/or T cell-mediated immune response. A peptide, protein or derivative used according to the invention can also comprise several such sequences, which represent epitopes for antibodies or T cells.

A part, i.e. fragment, of a nucleic acid that codes for a protein or peptide preferably refers according to the invention to the part of the nucleic acid that codes at least for the protein or peptide and/or for a part of the protein or peptide as defined above. A part of a nucleic acid that codes for a protein or peptide preferably refers to the part of the nucleic acid that corresponds to the open reading frame.

The pharmaceutical preparations and compositions described according to the invention can be used therapeutically for the treatment of an already existing disease or preventively/prophylactically as vaccines for immunization, to prevent the diseases described here.

Animal models can be used for testing an immunizing action e.g. against cancer when using a tumor-associated antigen as antigen. In this, for example human cancer cells can be introduced into a mouse to create a tumor and a preparation according to the invention or a composition according to the invention, comprising an RNA coding for a tumor-associated antigen, can be administered. The effect on the cancer cells (for example decrease in tumor size) can be measured as a measure for the efficacy of an immunization.

One or more vaccine-RNAs with one or more adjuvants for inducing an immune response or increasing an immune response can be administered as part of the composition for an immunization.

Other substances that stimulate a patient's immune response can also be administered. For example, cytokines can be used in a vaccination owing to their regulatory properties on lymphocytes. Said cytokines comprise e.g. interleukin-12 (IL-12), which has been shown to intensify the protective effects of vaccines (cf. Science 268:1432-1434, 1995), GM-CSF and IL-18.

The method according to the invention for inducing an immune response in a mammal generally comprises the administration of an amount of a vaccine-RNA which, together with the administration of Flt3 ligand, elicits an immune response, which preferably is prophylactic and/or therapeutic.

The term "transfection" refers according to the invention to the introduction of one or more nucleic acids into an organism or into a host cell. Various methods can be used according to the invention for introducing nucleic acids into cells in vitro or in vivo. Such methods comprise the transfection of nucleic acid-CaPO4 precipitates, the transfection of nucleic acids that are associated with DEAF, transfection or infection with viruses carrying the nucleic acids of interest, liposome-mediated transfection and similar. In particular embodiments, directing of the nucleic acid to particular cells is preferred. In those embodiments, a carrier that is used for the administration of a nucleic acid to a cell (e.g. a retrovirus or a liposome) can have a bound targeting molecule. For example, a molecule such as an antibody, which is specific to a surface membrane protein on the target cell, or a ligand for a receptor on the target cell, can be incorporated in the nucleic acid carrier or bound to it. If administration of a nucleic acid by liposomes is desired, proteins that bind to a surface membrane protein that is associated with endocytosis can be incorporated in the liposome formulation, in order to make targeting and/or uptake possible. Said proteins comprise capsid proteins or fragments thereof, which are specific to a particular cell type, antibodies to proteins that are internalized, proteins that target an intracellular site, and similar.

According to the invention, administration of nucleic acids can either take place as naked nucleic acid or in conjunction with an administration reagent. For example, administration of nucleic acids in vivo by means of targeted liposomes is also envisaged according to the invention.

For administration of nucleic acids, it is possible to use vectors derived from adenovirus (AV), adeno-associated virus (AAV), retroviruses (such as lentiviruses (LV), rhabdoviruses, murine leukemia virus), or herpesvirus, and the like. The tropism of the viral vectors can be suitably modified by pseudotyping of the vectors with coat proteins or other surface antigens from other viruses or by substitution of various viral capsid proteins.

Liposomes can support the supply of the nucleic acid to a particular tissue and can also increase the half-life of the nucleic acid. Liposomes that are suitable according to the invention are formed from standard vesicle-forming lipids, which generally include neutral or negatively charged phospholipids, and a sterol such as cholesterol. The selection of lipids is generally determined by factors such as the desired liposome size and the half-life of the liposomes. Many methods are known for production of liposomes; cf. e.g. Szoka et al. (1980), Ann. Rev. Biophys. Bioeng. 9: 467; and U.S. Pat. No. 4,235,871, U.S. Pat. No. 4,501,728, U.S. Pat. No. 4,837,028 and U.S. Pat. No. 5,019,369.

In particular embodiments, directing of the nucleic acid to particular cells is preferred. In those embodiments, a carrier that is used for the administration of a nucleic acid to a cell (e.g. a retrovirus or a liposome) can have a bound targeting molecule. For example, a molecule such as an antibody, which is specific to a surface membrane protein on the target cell, or a ligand for a receptor on the target cell can be incorporated in the nucleic acid carrier or can be bound to it. If administration of a nucleic acid by liposomes is desired, proteins that bind to a surface membrane protein that is associated with endocytosis can be incorporated in the liposome formulation, to make targeting and/or uptake possible. Said proteins comprise capsid proteins or fragments thereof, which are specific to a particular cell type, antibodies to proteins that are internalized, proteins that target an intracellular site, and the like.

Preferably, RNA is administered together with stabilizing substances such as RNase inhibitors.

Administration of polypeptides and peptides can take place in a manner known per se.

The term "patient", "individual" or "organism" refers to mammals. For example, mammals that are envisaged according to the invention are humans, primates, pets such as dogs, cats etc., domesticated animals such as sheep, cattle, goats, hogs, horses and the like, laboratory animals such as mice, rats, rabbits, guinea pigs etc., and animals kept in captivity such as zoo animals. The term "animal" as used herein includes humans.

Terms such as "raise", "increase" or "intensify" preferably refer to a raising, increase or intensification by at least 10%, in particular at least 20%, at least 50% or at least 100% respectively from a state that is not present and/or is not detectable to a state that is present and/or detectable.

The terms "T cell" and "T lymphocyte" are used interchangeably here and comprise helper T cells and cytolytic T cells such as cytotoxic T cells.

"Decrease" or "inhibit" refers here to the ability to bring about a decrease, such as a decrease by 20% or more, more preferably of 50% or more, and most preferably of 75% or more.

Immunization protocols using Flt3 ligand refer to the administration of Flt3 ligand and RNA, either mixed together or separately, optionally in combination with one or more excipients and other accompanying molecules and/or formulations (such as diluents, vehicles, excipients and the like) to an organism for the prevention and/or treatment of a disease or an infection. The Flt3 ligand and the RNA and any other constituents described herein can be administered in any dose, order, frequency and temporal arrangements. A person skilled in the art will appreciate that these parameters can routinely be altered by a person skilled in the art for optimizing a treatment.

The pharmaceutical compositions according to the invention, which contain vaccine-RNA, Flt3 ligand or both, are preferably administered in pharmaceutically compatible preparations. Said preparations can usually contain pharmaceutically compatible concentrations of salts, buffers, preservatives, excipients, supplementary immunity-increasing substances such as adjuvants (e.g. CpG-oligonucleotides) and cytokines and optionally therapeutic active substances.

The pharmaceutical compositions according to the invention can be administered by any conventional route, including by injection or by infusion. Administration can for example take place orally, intravenously, intraperitoneally, intramuscularly, subcutaneously, intracutaneously, transdermally, intralymphatically, preferably by injection into lymph nodes, in particular inguinal lymph nodes, lymphatic vessels and/or into the spleen.

The RNA and Flt3 ligand can be administered separately from one another, i.e. in different compositions, or in a common composition. If administered separately from one another, the administration of RNA and Flt3 ligand can take place simultaneously or at different timepoints, and the RNA and/or Flt3 ligand can be administered repeatedly. If the administration of RNA and Flt3 ligand takes place at different timepoints, the time interval between the administrations or in the case of repeated administration between the last administrations of RNA or Flt3 ligand and the first administration of the respectively remaining constituent can be 6 hours or more, 12 hours or more, 24 hours or more, 2 days or more, 3 days or more, 5 days or more, 7 days or more or 9 days or more. Preferably the time interval between the administrations is not more than 24 hours, not more than 2 days, not more than 4 days, not more than 8 days or not more than 10 days. Preferably the Flt3 ligand is administered prior to administration of RNA. If the RNA and Flt3 ligand are administered separately from one another, the RNA is preferably administered intralymphatically, more preferably intranodally, and the Flt3 ligand is preferably administered intravenously, intraperitoneally, intramuscularly, subcutaneously, intracutaneously or transdermally, preferably intraperitoneally or subcutaneously.

The compositions according to the invention are administered in effective amounts. An "effective amount" refers to the amount which, alone or together with further doses, achieves a desired reaction or a desired effect. In the case of treatment of a particular disease or a particular state, the desired reaction refers to inhibition of the disease process. This comprises slowing the progression of the disease and in particular interruption of the progression of the disease. The desired reaction in a treatment of a disease or of a state can also be delaying the onset or preventing the onset of the disease or of the state.

An effective amount of a composition according to the invention will depend on the condition to be treated, the severity of the disease, the patient's individual parameters, including age, physiological state, height and weight, the duration of the treatment, the type of concomitant therapy (if present), the specific route of administration and similar factors.

The pharmaceutical compositions according to the invention are preferably sterile and contain an effective amount of the active substance for producing the desired reaction or the desired effect.

The doses of the compositions according to the invention that are administered can depend on various parameters such as the mode of administration, the patient's condition, the desired period of administration, etc. In the case when a patient's reaction is insufficient at an initial dose, higher doses (or effectively higher doses, which are achieved by another, more localized route of administration) can be used.

Generally, for a treatment or for producing or increasing an immune response, preferably doses of the RNA from 1 ng to 700 μg, 1 ng to 500 μg, 1 ng to 300 μg, 1 ng to 200 μg, or 1 ng to 100 μg are formulated and administered.

The pharmaceutical compositions according to the invention are generally administered in pharmaceutically compatible amounts and in pharmaceutically compatible compositions. Said compositions can usually contain salts, buffers, preservatives, excipients and optionally therapeutic active substances. When used in medicine, the salts should be pharmaceutically compatible. Salts that are not pharmaceutically compatible can, however, be used for the production of pharmaceutically compatible salts thereof and are included according to the invention. These pharmacologically and pharmaceutically compatible salts comprise, but are not limited to, those that are produced from the following acids: hydrochloric, hydrobromic, sulfuric, nitric, phosphoric, maleic, acetic, salicylic, citric, formic, malonic, succinic acid and the like. Pharmaceutically compatible salts can also be produced as salts of alkali metals or alkaline earth metals such as sodium, potassium or calcium salts.

A pharmaceutical composition according to the invention can comprise a pharmaceutically compatible excipient. The term "pharmaceutically compatible excipient" refers according to the invention to one or more compatible solid or liquid fillers, diluents or capsule substances that are suitable for administration to a human. The term "excipient" refers to an organic or inorganic constituent, natural or synthetic, in which the active constituent is combined, in order to facilitate application. The constituents of the pharmaceutical composition according to the invention are usually such that no interaction occurs that substantially impairs the desired pharmaceutical efficacy.

Preferably the excipients are sterile liquids such as water or oils, including those derived from petroleum, animals or plants or are of synthetic origin, for example peanut oil, soybean oil, mineral oil, sesame oil, sunflower oil and the like. Salt solutions and aqueous dextrose and glycerol solutions can also be used as aqueous excipients.

Examples of excipients are acrylic and methacrylic derivatives, alginic acid, sorbic acid derivatives such as α-octadecyl-ω-hydroxypoly(oxyethylene)-5-sorbic acid, amino acids and derivatives thereof, in particular amino compounds such as choline, lecithin and phosphatidylcholine, gum arabic, aroma substances, ascorbic acid, carbonates such as for example carbonates and hydrogen carbonates of sodium, potassium, magnesium and calcium, hydrogen phosphates and phosphates of sodium, potassium, calcium and magnesium, carmellose sodium, dimethicone, colorants, flavorings, buffers, preservatives, thickeners, plasticizers, gelatin, glucose syrups, malt, finely divided silica, hydromellose, benzoates, in particular sodium and potassium benzoate, macrogol, skim milk powder, magnesium oxide, fatty acids and derivatives thereof and salts such as stearic acid and stearates, in particular magnesium and calcium stearate, fatty acid esters and mono- and diglycerides of edible fatty acids, natural and artificial waxes such as beeswax, yellow wax and montan glycol wax, chlorides, in particular sodium chloride, polyvidone, polyethylene glycols, polyvinylpyrrolidone, povidone, oils such as castor oil, soya oil, coconut oil, palm kernel oil, sugars and sugar derivatives, in particular mono- and disaccharides such as glucose, fructose, mannose, galactose, lactose, maltose, xylose, sucrose, dextrose and cellulose and derivatives thereof, shellac, starch and starch derivatives, in particular corn starch, tallow, talc, titanium dioxide, tartaric acid, sugar alcohols such as glycerol, mannitol, sorbitol and xylitol and derivatives thereof, glycol, ethanol and mixtures thereof.

Preferably the pharmaceutical compositions can additionally also contain wetting agents, emulsifiers and/or pH-buffering agents.

In another embodiment the pharmaceutical compositions can contain an absorption enhancer. These absorption enhancers can, if desired, replace an equimolar amount of the vehicle in the composition Examples of said absorption enhancers comprise, but are not limited to, eucalyptol, N,N-diethyl-m-toluamide, polyoxyalkylene alcohols (such as propylene glycol and polyethylene glycol), N-methyl-2-pyrrolidone, isopropyl myristate, dimethylformamide (DMF), dimethylsulfoxide (DMSO), dimethylacetamide (DMA), urea, diethanolamine, triethanolamine and the like (see e.g. Percutaneous Penetration Enhancers, Ed. Smith et al. (CRC Press, 1995)). The amount of absorption enhancer in the composition may depend on the desired effects to be achieved.

A protease inhibitor can be incorporated in the composition according to the invention, in particular the composition containing Flt3 ligand, in order to prevent degradation of a peptide or protein active substance and thereby increase the bioavailability. Examples of protease inhibitors comprise, but are not limited to, aprotinin, leupepsin, pepstatin, α2-macroglobulin and trypsin-inhibitor. These inhibitors can be used alone or in combination.

The pharmaceutical compositions according to the invention can be provided with one or more coatings. Preferably the solid oral dosage forms are provided with an enteric coating or are in the form of an enteric, hardened soft-gelatin capsule.

The pharmaceutical compositions according to the invention can contain suitable buffers such as acetic acid in a salt, citric acid in a salt, boric acid in a salt and phosphoric acid in a salt.

The pharmaceutical compositions can also optionally contain suitable preservatives such as benzalkonium chloride, chlorobutanol, parabens and thimerosal.

The pharmaceutical compositions are usually supplied in a uniform dosage form and can be produced in a manner known per se. Pharmaceutical compositions according to the invention can for example be in the form of capsules, tablets, pastilles, solutions, suspensions, syrups, elixirs or as emulsion.

Compositions that are suitable for parenteral administration usually comprise a sterile aqueous or nonaqueous preparation, which preferably is isotonic with the recipient's blood. Compatible vehicles and solvents are for example Ringer solution and isotonic sodium chloride solution. In addition, sterile, fixed oils are usually employed as dissolving or suspending medium.

The present invention is explained in detail with the following examples and drawings, which serve exclusively for explanation and are not to be understood as limiting. Based on the description and the examples, further embodiments will be accessible by a person skilled in the art, which do not go beyond the scope of the invention and the scope of the appended claims.

Figure 1:
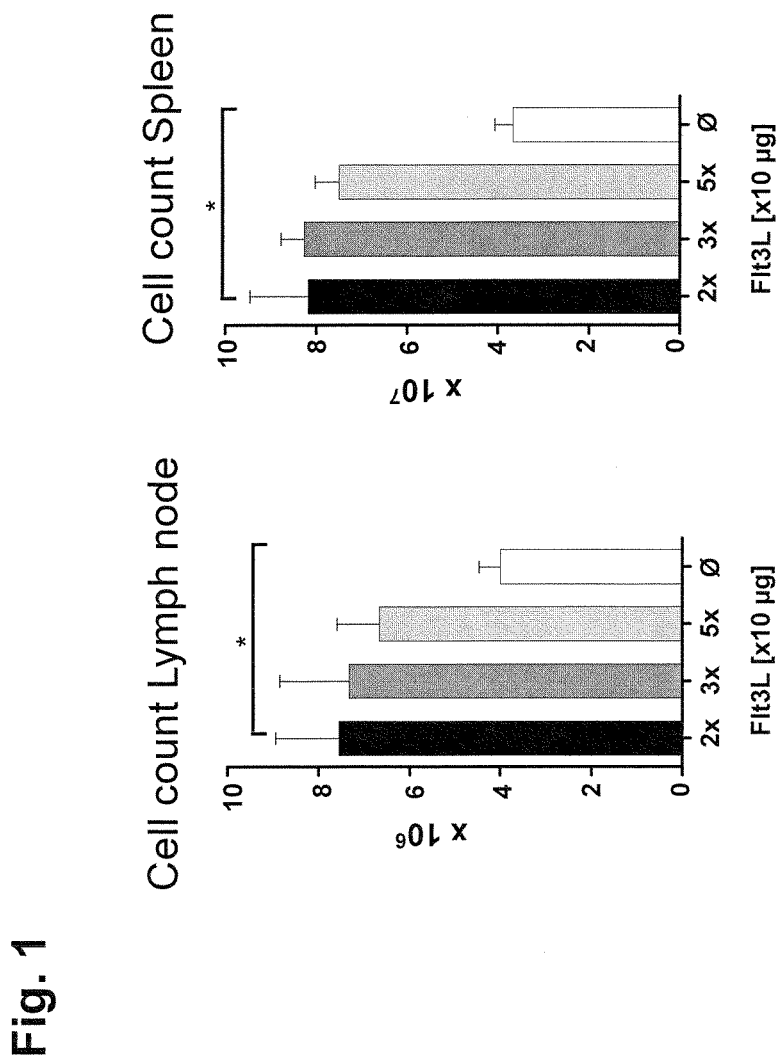
FIG. 1:
C57Bl/6 mice (n=3-9) were administered 10 µg Flt3L intraperitoneally at different timepoints (d1 to d3 or d1, d1, d3 or d0, d3). On day 10 the lymph nodes (LN) and the spleen were removed and the cell count was determined. The data shown represent the average cell count +SEM of the lymph nodes. *: $p<0.05$ in Tukey's multiple comparison test.

(a) The frequency of the epitope-specific T lymphocytes was quantified by flow cytometry after staining with a SIINFEKL-tetramer and anti-CD8 antibody. The data shown represent the average number and average frequency of tetramer-positive CD8+ T lymphocytes +SEM.

(b) For measuring the IFNγ-producing SIINFEKL-specific T lymphocytes, spleen cells were incubated with SIINFEKL-peptide or control peptide for 6 h. Brefeldin A was added [10 µg/ml] after 1.5 h. After fixing and permeabilization, the samples were stained with anti-CD8 and anti-IFNγ antibodies. The data shown represent the frequency of SIINFEKL-specific IFNγ-secreting CD8+ T lymphocytes after subtracting the nonspecific background +SEM. *: p<0.05 in the two-sided unpaired t-test.

(c) Representative dot-plots. The percentages shown indicate the respective frequency of tetramer-positive CD8+ T lymphocytes.

FIG. 5:

(a) Balb/c mice (n=5) were injected intranodally either with 10 µg Cy3-fluorophore labeled RNA (red) or with pure Cy3-ribonucleotide (control). Lymph nodes were removed after 5 and 30 min, fixed with paraformaldehyde and sectioned. Whereas control lymph nodes show a minimal background, otherwise a cellular RNA signal can be discerned, which increases in clarity from 5 minutes to 30 minutes. This can be attributed to destruction of intercellular RNA.

(b) Human immature DCs (iDCs) were coincubated in vitro with Cy3-fluorophore labeled RNA (5 µg, red) and FITC-dextran (1 µg/µl, green) for 10 min, fixed with paraformaldehyde and counterstained (Hoechst 33342, blue). The temporal kinetics shows, as in maximal colocalization with FITC-dextran, the RNA is initially localized in the periphery of the cell, then the vesicles can be seen in the whole cytoplasm and finally coalesce in larger structures.

FIG. 6:

(a) Human iDCs (n=3) were coincubated in vitro at various temperatures with luciferase-RNA (20 µg) for 15 min. After 24 h the luciferase signal was quantified in a standard luminescence test. The result indicates an active energy-consuming process.

(b-c) Human iDCs were pretreated with various inhibitors (dimethyl amiloride, cytochalasin D, LY294002, Rottlerin) and then coincubated for 15 min with luciferase-RNA or Cy3-RNA. After 24 h the luciferase signal was quantified in a standard luminescence test. It was found that with the highly specific macropinocytosis inhibitor Rottlerin there is inhibition of RNA uptake to more than 90%.

(d) The inguinal lymph nodes of C57Bl/6 mice were pretreated in vivo with Rottlerin (10 µl [10 µM]) and then luciferase-RNA (10 µg) was injected intranodally: After in vivo inhibition of macropinocytosis, RNA uptake in the lymph nodes is drastically reduced.

(e) C57Bl/6 mice (n=3) were immunized intranodally on d0 and d3 with SIINFEKL-coding RNA (20 µg). On both days the lymph nodes were pretreated with Rottlerin as described above. On day 8 the success of immunization was quantified by tetramer measurement in the peripheral blood. The success of intranodal RNA immunization correlated directly with the ability of cells to take up RNA by macropinocytosis.

*, P<0.05; , P<0.01; *, P<0.001; (ANOVA with Tukey's multiple comparison test).

FIG. 7:

(a-d) Human (a, c) and murine (b, d) DCs were matured for 40 hours with various agents (Poly I:C (50 µg/ml), CD40L (1.0 µg/ml), LPS (20 µg/ml), Mat. Mix (TNFalpha (10 ng/ml), IL1b (10 ng/ml), PGE (1 µg/ml), IL6 (1000 U/ml)). Then the cells were coincubated for 15 min with luciferase-RNA or Cy3-RNA. After 24 h the luciferase signal was quantified in a standard luminescence test. For quantifying the uptake of Cy3-RNA, the cells were washed and fixed 30 minutes after incubation with the RNA. After that, the Cy3-mediated fluorescence could be quantified in the immunofluorescence microscope (Till Vision Software 4.0, Till Photonics). After maturation of the iDCs, the RNA uptake is reduced by more than 90%.

(e) Effect of Poly I:C on RNA uptake. C57Bl/6 mice (n=4) were injected s.c. with PBS or Poly I:C (20 µg) and after 2 or 24 h, luciferase-RNA was applied intranodally. After 24 h the luciferase signal was quantified in a standard bioluminescence test. There is a sharp reduction in RNA uptake, depending on the time interval after administration of adjuvant.

*, P<0.05; , P<0.01; *, P<0.001; (ANOVA with Tukey's multiple comparison test).

(f) Effect of Flt3-L on RNA uptake. C57BL/6 mice (n=8) were treated i.p. on day 0 and 3 with 10 µg, Flt3-L, or were not treated in the control group. On day 10 the mice were injected intranodally with 20 µg luciferase-RNA. 24 h later the luciferase signal was measured by in-vivo bioluminescence. Administration of Flt3-L does not have an inhibitory effect on RNA uptake in the lymph nodes.

FIG. 8:

C57BL/6 mice (n=5) were intraperitoneally injected on day 0 Flt3L-IgG4, Flt3L (Humanzyme), Flt3L (Peprotech) or human IgG4 in an amount of 0.4 mol. On day 10 the lymph nodes of the mice were removed and characterized by flow cytometry. Dendritic cells (DCs (marker: CD11c+/NK1.1−)), CD4+ helper T cells (marker: CD3+/CD4+/CD8−/NK1.1−), CD8+ T cells (marker: CD3+/CD8+/CD4−/NK1.1−), CD19+ B cells (marker: CD19+/CD3−/NK1.1−).

FIG. 9:

Naïve C57BL/6 mice (n=7) were intraperitoneally injected on day 0, +3 Flt3L (Flt3L-IgG4, Flt3L (Humanzyme), Flt3L (Peprotech)) or human IgG4 in an amount of 0.4 mol. These mice were immunized intralymphatically on day +7, +10 with 20 µg SIINFEKL coding RNA. The control group remained untreated (n=2). On day +15 the frequency of antigen-specific CD8+ T lymphocytes was measured in peripheral blood by means of MHC multimer measurement.

Figure 10:
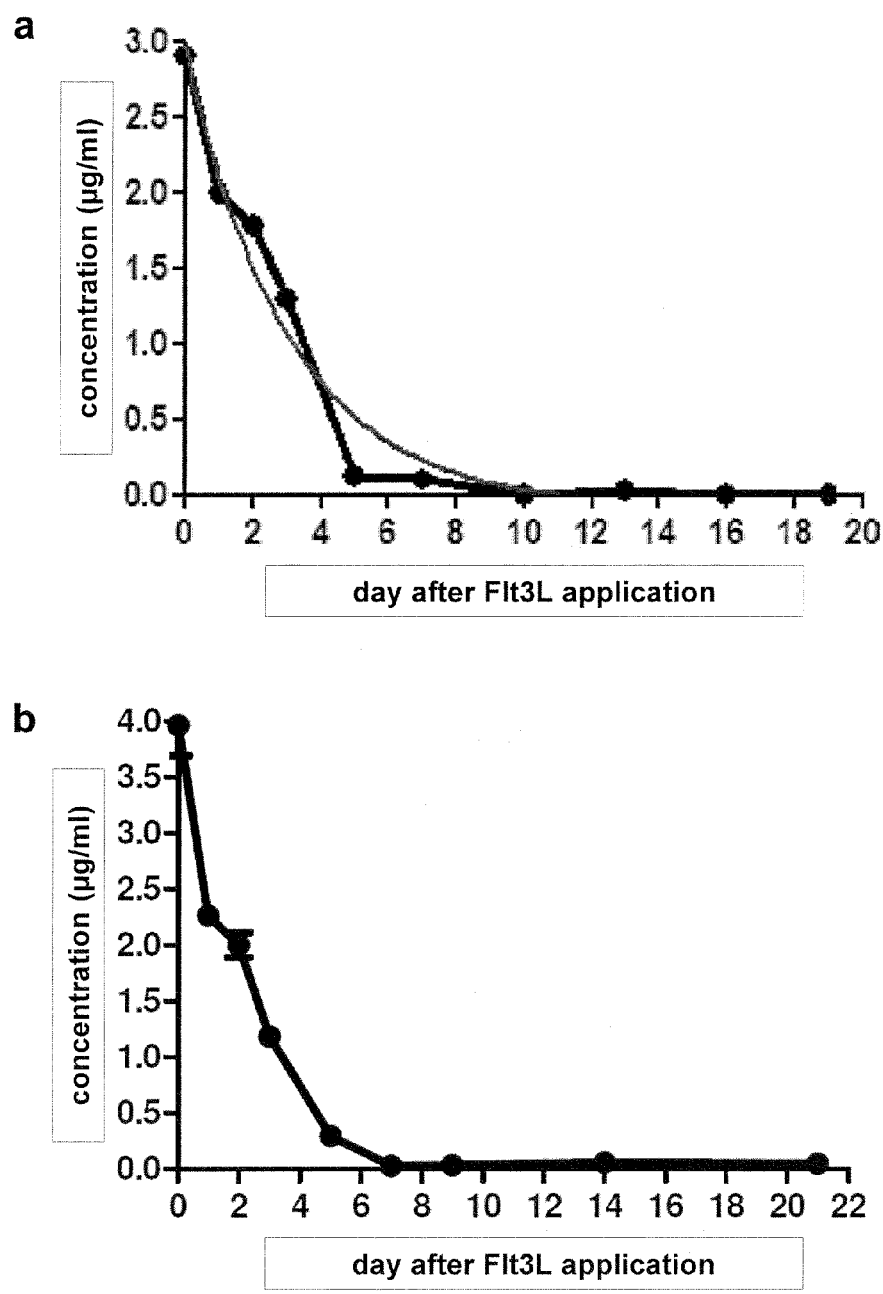

FIG. 10: Temporal kinetics of Flt3L-IgG4 in serum of mice.

(a) Balb/c mice (n=3) were i.p. administered 20 µg Flt3L-IgG4. At defined time points (prior to administration; 3 h, 24 h, 48 h, 3 d, 5 d, 7 d, 9 d, 14 d, 21 d) serum samples of the mice were preserved. These samples were used in an ELISA assay for quantifying human IgG. The half-time is 2.14 days (=51 hours).

(b) Balb/c mice (n=3) were i.p. administered 50 µg Flt3L-IgG4. At defined time points (prior to administration; 3 h, 24 h, 48 h, 3 d, 5 d, 7 d, 9 d, 14 d, 21 d) serum samples of the mice were preserved. These samples were used in an ELISA assay for quantifying human IgG. The half-time is 1,667 days (=40 hours).

Figure 11:
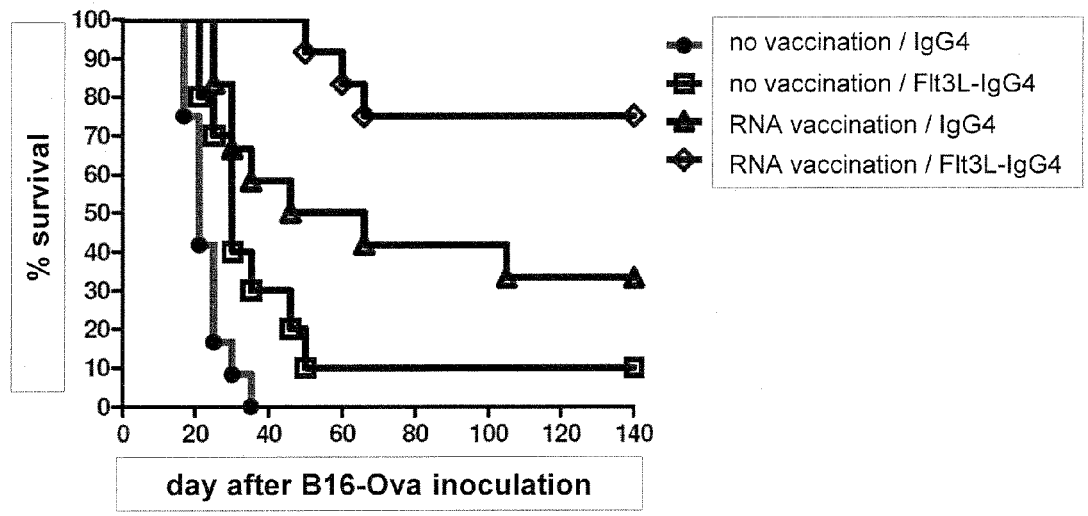

FIG. 11: Therapeutic vaccination against B16 Ova tumors.

To examine the synergy of combining Flt3L administration with RNA vaccination, a therapeutic tumor experiment was performed. To this end, 4 groups (n=10) of C57BL/6 mice were formed. All mice received on day 0 a s.c. injection of B16 Ova cells (2×10$^5$). Hereof a control group was only treated by IgG4 injection (10 µg; d3, d7, d14, d17). A second control group received only Flt3L-IgG4 injections (15 µg; d3, d7, d14, d17). The first therapy group was treated by intranodal injection of SIINFEKL coding RNA (20 µg; d11, d14, d17, d24) in combination with administration of IgG4 and the second therapy group received Flt3L-IgG4 as described above for RNA immunization. The Kaplan Meier plot of the survival rate of mice is shown. Mice were sacrificed if they had a tumor diameter of >1.5 cm in one axis.

Figure 12:
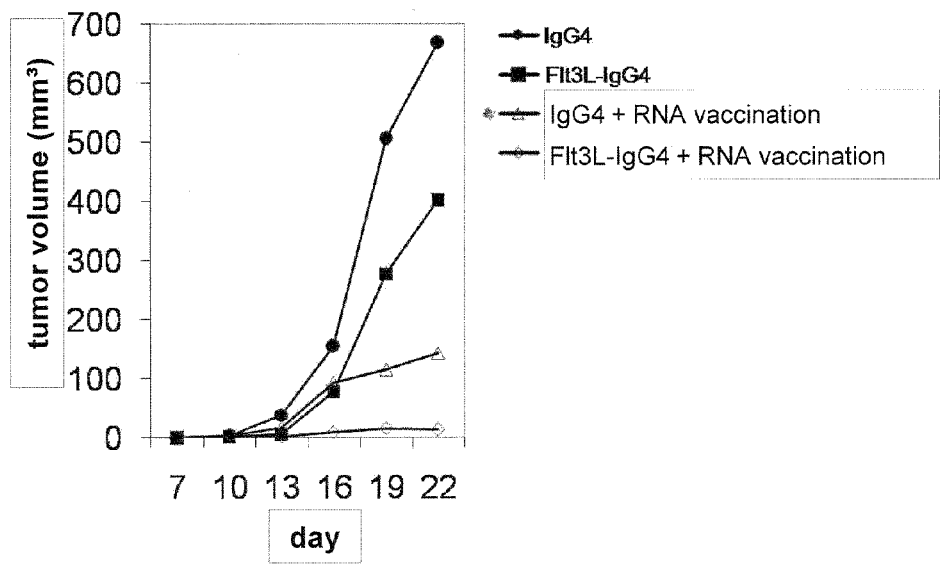

FIG. 12: Therapeutic vaccination against B16 Ova tumors.

Examination of tumor growth. To this end, four groups (n=10) of C57BL/6 mice were formed. All mice received on day 0 a s.c. injection of B16 Ova tumor cells ($2\times10^5$). Hereof a control group was only treated by IgG4 injection (15 µg; d3, d7, d14, d18). A second control group received only Flt3L-IgG4 injections (15 µg; d3, d7, d14, d18). The first therapy group was treated by intranodal injection of SIINFEKL coding RNA (20 µg; d10, d14, d18, d21) in combination with administration of IgG4 and the second therapy group received Flt3L-IgG4 as described above for RNA immunization. The tumor volume was determined after tumor inoculation on a regular basis (d7, d10, d13, d16, d19, d22). The average tumor volume [$mm^3$] on the days following tumor inoculation [day] is shown.

EXAMPLES

Example 1

The recombinant human Flt3 ligand used in this example and in the following examples was prepared as a fusion protein with IgG4 and had the sequence shown in SEQ ID NO: 6. To this end, the nucleic acid sequence coding for the Flt3L-IgG4 fusion protein was cloned into an expression vector. The resulting plasmid was transfected into HEK293 cells (ATCC No. CRL-1573) by means of lipofection. The supernatant was collected and purified over a protein A column (GE HiTrap MabSelect SuRe, GE Healthcare) according to the manufacturer's instructions. The product was dialyzed against PBS, aliquoted and frozen until use.

Figure 2:
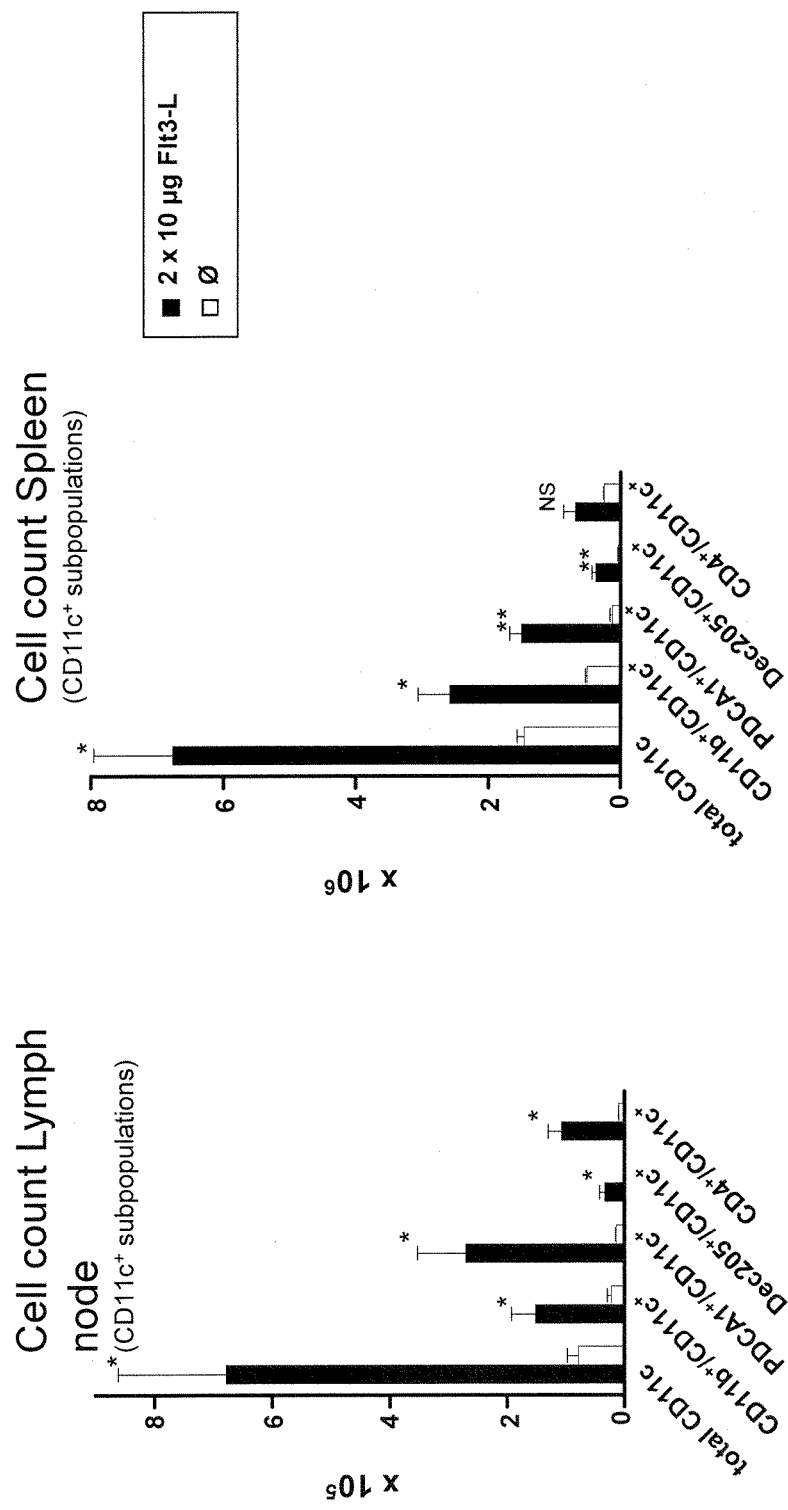
FIG. 2:
C57Bl/6 mice (n=3) were administered 10 µg Flt3L twice (d0, d3) intraperitoneally. On day 10 the inguinal lymph nodes were removed, the cells were stained with corresponding antibodies and the subpopulations of the dendritic cells were quantified by flow cytometry. The data shown represent the average cell count of the subpopulation *: $p<0.05$ and **: $p<0.001$ in the two-sided unpaired t-test.

To test the effects of application of human Flt3 ligand on the efficiency of RNA-based immunizations, the changes in the cellular composition of lymph nodes and spleen were first investigated in the mouse model. For this, various application schemes (2×, 3×, 5×10 µg) of recombinant Flt3-L were applied intraperitoneally and the cellularity was determined 10-12 days after the first injection. As is described in the literature for the mouse system, we were able to show (FIG. 1) that there is an increase in cellularity in spleen and lymph nodes (Lyman, S. D. et al. (1994) Blood 83:2795-2801, Hannum, C. et al. (1994) Nature 368:643-648, Maraskovsky, E. et al. (1996) Journal of Experimental Medicine 184:1953-1962). Moreover, it was found (FIG. 2), in agreement with published data for the mouse and for humans, that the application of Flt3-L at various doses leads to an increase in dendritic cells (Maraskovsky, E. et al. (1996) Journal of Experimental Medicine 184:1953-1962, McNeel, D. G. et al. (2003) Journal of Clinical Immunology 23:62-72, Freedman, R. S. et al. (2003) Clinical Cancer Research 9:5228-5237, Maraskovsky, E. et al. (2000) Blood 96:878-884). This increase could be shown for all relevant subpopulations of the dendritic cells in spleen and lymph nodes (FIG. 2).

Example 2

Figure 3:
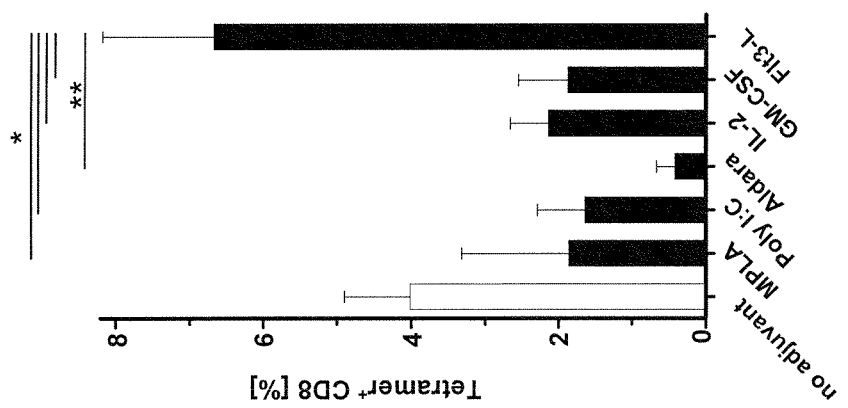
FIG. 3:
Anesthetized C57Bl/6 mice (n=5) were administered twice (d0, d3) in each case 20 µg SIINFEKL coding RNA in the inguinal lymph nodes. Various adjuvants were administered to the mice (MPLA d0+d3, 20 µg s.c.; Poly I:C d0+d3, 20 µg s.c.; Aldara Creme d0+d3, 5 µg transcutaneously; GM-CSF −d2, −d1, d1, d2, 5 µg s.c; IL-2 (Proleukin) d1-d6, 80000 IU s.c.; Flt3-L d-7+d-4, 10 µg i.p.). On day 8 blood was taken from the mice and the frequency of the epitope-specific T lymphocytes was quantified by flow cytometry after staining with a SIINFEKL-tetramer and anti-CD8 antibody. The data shown represent the average frequency of tetramer-positive CD8+T lymphocytes +SEM from 2 experiments. *: $p<0.05$ and **: $p<0.001$ in Tukey's multiple comparison test.

Next we investigated the effects of various known adjuvants (Aldara, monophosphoryl lipid A, GM-CSF, Poly I:C, IL2) and Flt3-L on the priming of naive T cells and their frequency in the peripheral blood after intranodal RNA immunization. For this purpose the adjuvants were applied s.c. or i.p. (see legend of FIG. 3 for details) and the mice were immunized twice, with an interval of 3 days, with an RNA coding for the $H-2K^b$ restricted SIINFEKL epitope. Five days after the second immunization, the frequency of the epitope-specific CD8+ T cells was quantified by tetramer measurement in the blood. To our astonishment, the analysis showed that all adjuvants except Flt3-L led to a reduction in efficiency of T cell priming (FIG. 3). For the use of adjuvants in the setting of the application of naked IVT-RNA, to date only the aforementioned work has been published, in which it was shown that only the administration of GM-CSF after intradermal RNA-injection, in contrast to administration beforehand, offers an advantage over RNA-injection alone (Carralot, J. P. et al. (2004) Cell Mol. Life. Sci. 61:2418-2424). These data are in agreement with our experiments, in which GM-CSF was applied before the RNA immunization (−48 h, −24 h). Furthermore, our data show for the first time that established adjuvants tend to lead to impairment of the efficiency of T cell priming, whereas Flt3-L induces a significant increase (FIG. 3). Further tetramer analyses from peripheral blood 7 days after the last immunization showed similar results (data not shown).

Example 3

Figure 4:
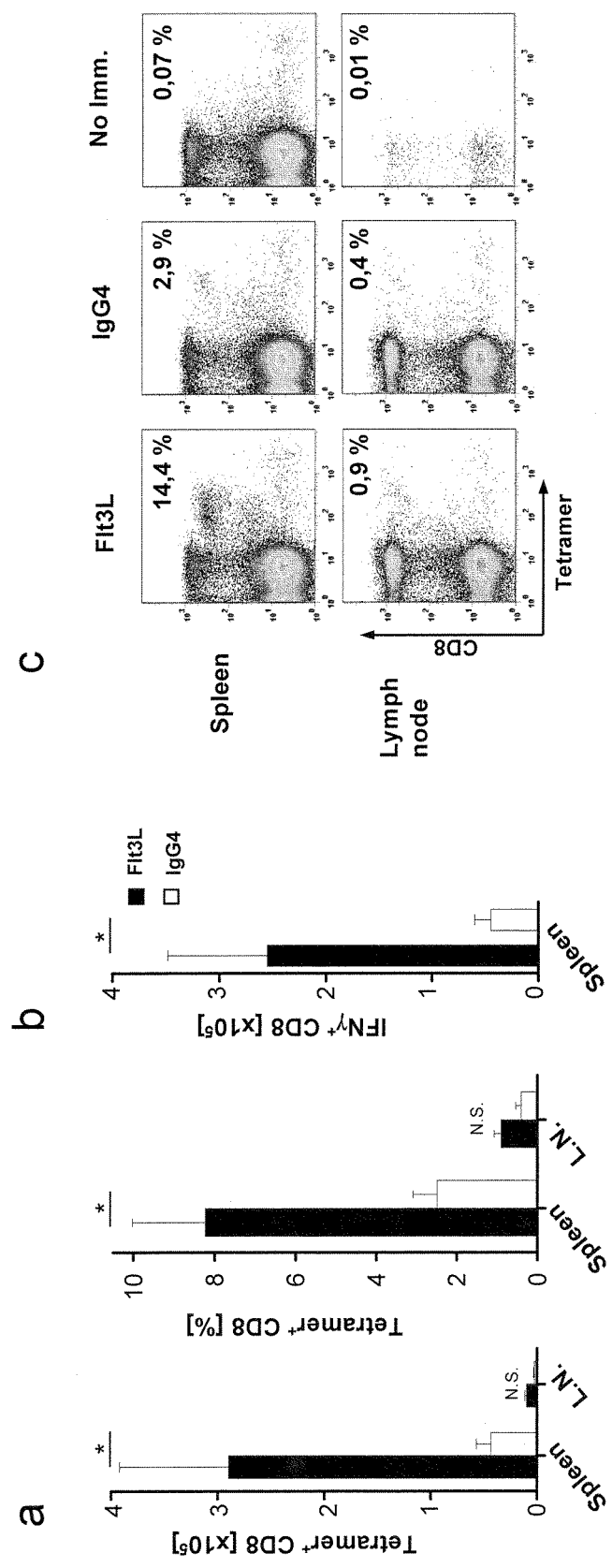
FIG. 4:
C57Bl/6 mice (n=4) were administered 10 µg Flt3L or human IgG4 twice (d0, d3) intraperitoneally. On days 7 and 10 the anesthetized mice were on each occasion administered 20 µg SIINFEKL-coding RNA in the inguinal lymph nodes. On day 15 the spleen and the inguinal lymph nodes were removed.

In further experiments, we were able to show that the administration of human Flt3-L leads to a significant increase in the frequency of antigen-specific functional T cells after intranodal RNA immunization in other organs (spleen) as well. For this, mice were injected intraperitoneally on day 0 and day 3 in each case with 10 µg Flt3-L or human IgG4. Intranodal immunization with SIINFEKL-coding RNA was then carried out on day 7 and 10. On day 15 the frequency of the epitope-specific CD8+ T cells was quantified by tetramer measurement and determination of intracellular cytokine (FIG. 4). The tetramer quantification showed a significantly increased frequency of epitope-specific CD8+ T cells in the group pretreated with Flt3-L (spleen: 8.2% vs 2.5%). On the functional level, it was shown that these cells are also able to secrete IFNγ (FIG. 4). Further investigations showed that increases in the dose of Flt3-L above the dose of 2×10 µg are not correlated with a further intensification of the immune response (data not shown).

Example 4

Figure 5:
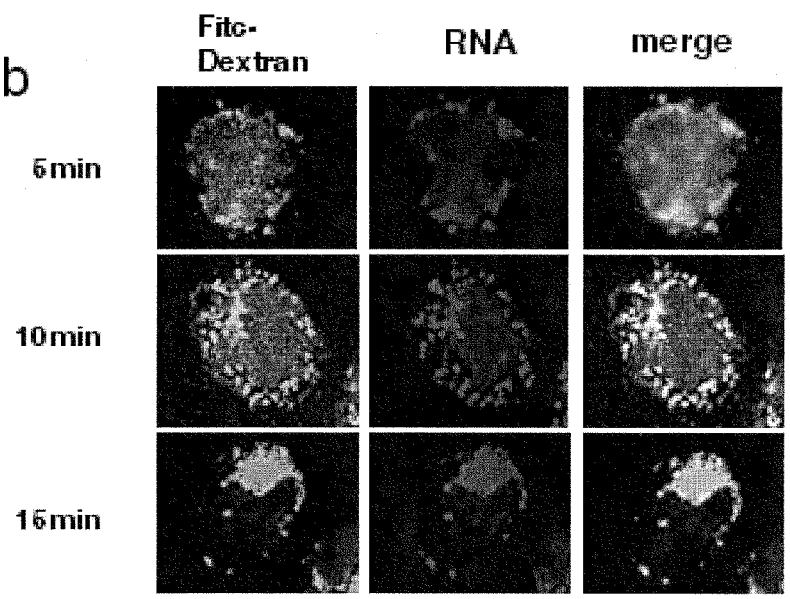

Balb/c mice (n=5) were injected intranodally either with 10 µg Cy3-fluorophore-labeled RNA or with pure Cy3-ribonucleotide (control). After 5 or 30 minutes, lymph nodes were removed and cryostat sections were evaluated by immunofluorescence microscopy after paraformaldehyde fixation. The representative sections shown in FIG. 5 show a minimal background in the control lymph nodes and a cellular RNA signal (red) which gains in clarity from 5 minutes to 30 minutes. This can be attributed to the destruction of intercellular RNA.

In addition, human immature DCs were coincubated in vitro with Cy3-fluorophore labeled RNA (5 µg, red) and FITC-dextran (1 µg/µl, green) for 10 min, fixed with paraformaldehyde and counterstained (Hoechst 33342, blue). The temporal kinetics shows, as in maximal colocalization with FITC-dextran, the RNA initially is localized in the periphery of the cell, then the vesicles can be seen in the whole cytoplasm and they finally coalesce in larger structures.

Therefore it was shown that naked RNA is taken up by cells both in vitro and in vivo.

Example 5

The phenomenon of lack of adjuvant action of some known adjuvants was investigated in more detail.

We found that naked RNA (i.e. dissolved in liquid e.g. PBS) after injection e.g. in lymph nodes is taken up almost exclusively by dendritic cells. The uptake is extraordinarily efficient. The RNA taken up is then translated.

Figure 6:
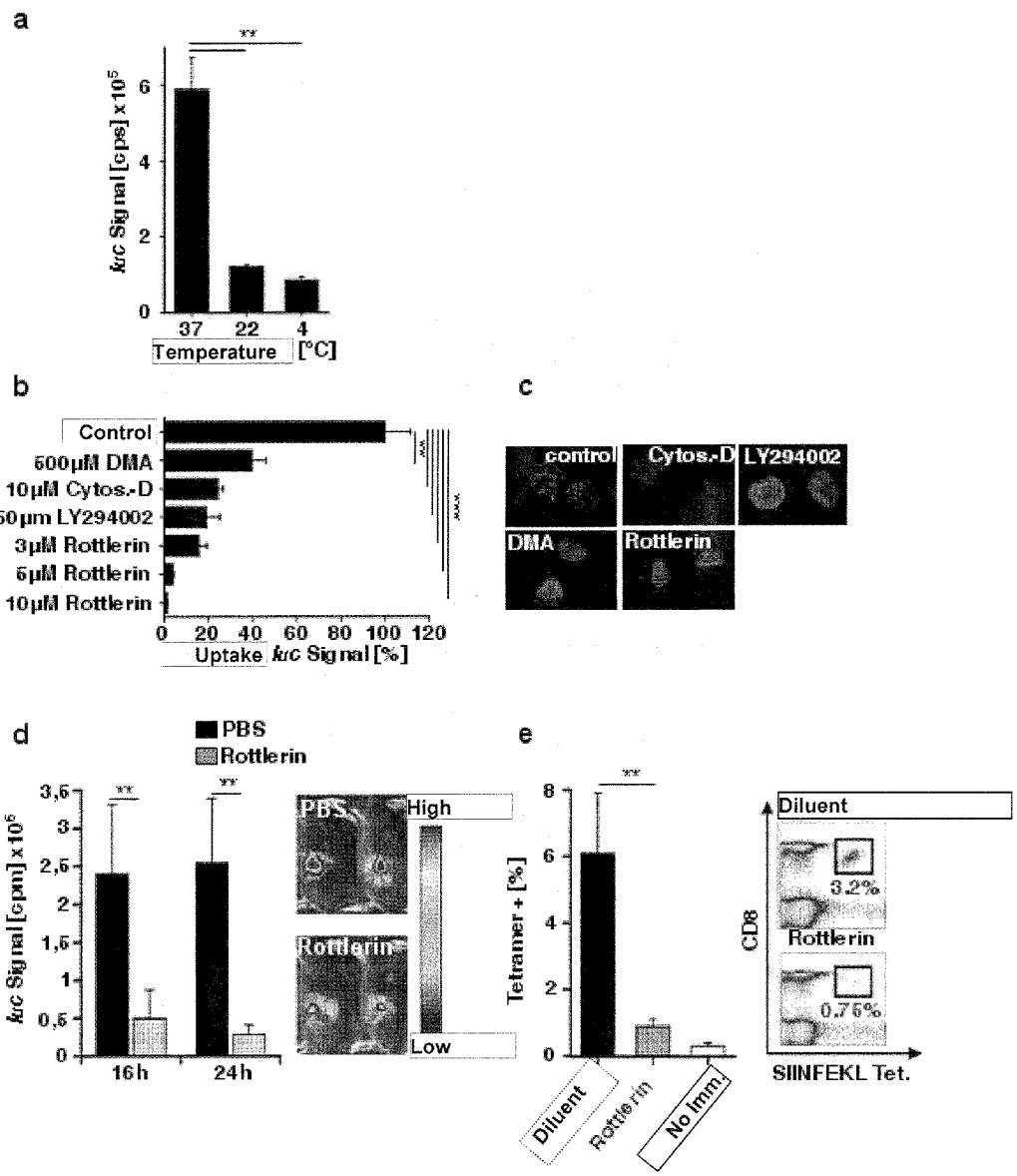

For more detailed characterization of the uptake process for naked RNA, human iDCs (n=3) were coincubated in vitro at various temperatures with luciferase-RNA (20 µg) for 15 min. After culture at 37° C. for a further 22 h, the RNA uptake was quantified in a luciferase test. The mean+SEM is shown. The result shown in FIG. 6(a) indicates an active energy-consuming process.

To verify whether the macropinocytosis constitutively active in iDCs is relevant for the uptake of naked RNA, human iDCs were pretreated with various inhibitors (dimethyl amiloride, cytochalasin D, LY294002, Rottlerin) and then coincubated for 15 min with luciferase-RNA or Cy3-RNA. After culture for a further 22 h, RNA uptake was quantified in a luciferase test. The mean+SEM is shown. The iDCs coincubated with Cy3-RNA (red) were fixed with paraformaldehyde and counterstained (Hoechst 33342, blue). It was found that with the highly specific macropinocytosis inhibitor Rottlerin, there is inhibition of RNA uptake to more than 90%; cf. FIG. 6(b-c).

To clarify whether macropinocytosis is also the uptake mechanism relevant in vivo for RNA in the lymph node, the inguinal lymph nodes of C57/B16 mice were pretreated with Rottlerin (n=4, 10 µM) and then luciferase-RNA (10 µg) was injected intranodally. After 24 h, the in-vivo bioluminescence signal was measured. The mean+SEM is shown in FIG. 6(d). We were able to show that after in vivo inhibition of macropinocytosis, RNA uptake in the lymph node is drastically reduced.

To verify whether the in vivo inhibition of macropinocytosis has an effect on the efficiency of T cell priming after intranodal RNA immunization, C57/B16 mice (n=3) were immunized intranodally on d0 and d3 with SIINFEKL-coding RNA (20 µg). On both days the lymph nodes were pretreated with Rottlerin as described above. The mean+SEM of the frequency of CD8+ antigen-specific T lymphocytes is shown. We were able to demonstrate that the success of intranodal RNA immunization is directly correlated with the ability of cells to take up RNA by macropinocytosis; cf. FIG. 6(e).

The main uptake mechanism of RNA uptake is macropinocytosis. Inhibition of macropinocytosis e.g. by chemicals that inhibit macropinocytosis (e.g. Rottlerin), leads to an almost complete loss of vaccine action.

Example 6

Next we investigated to what extent the maturation of iDCs, which is connected with a down-regulation of macropinocytosis, leads to a reduction of RNA uptake. The results are shown in FIG. 7.

Figure 7:
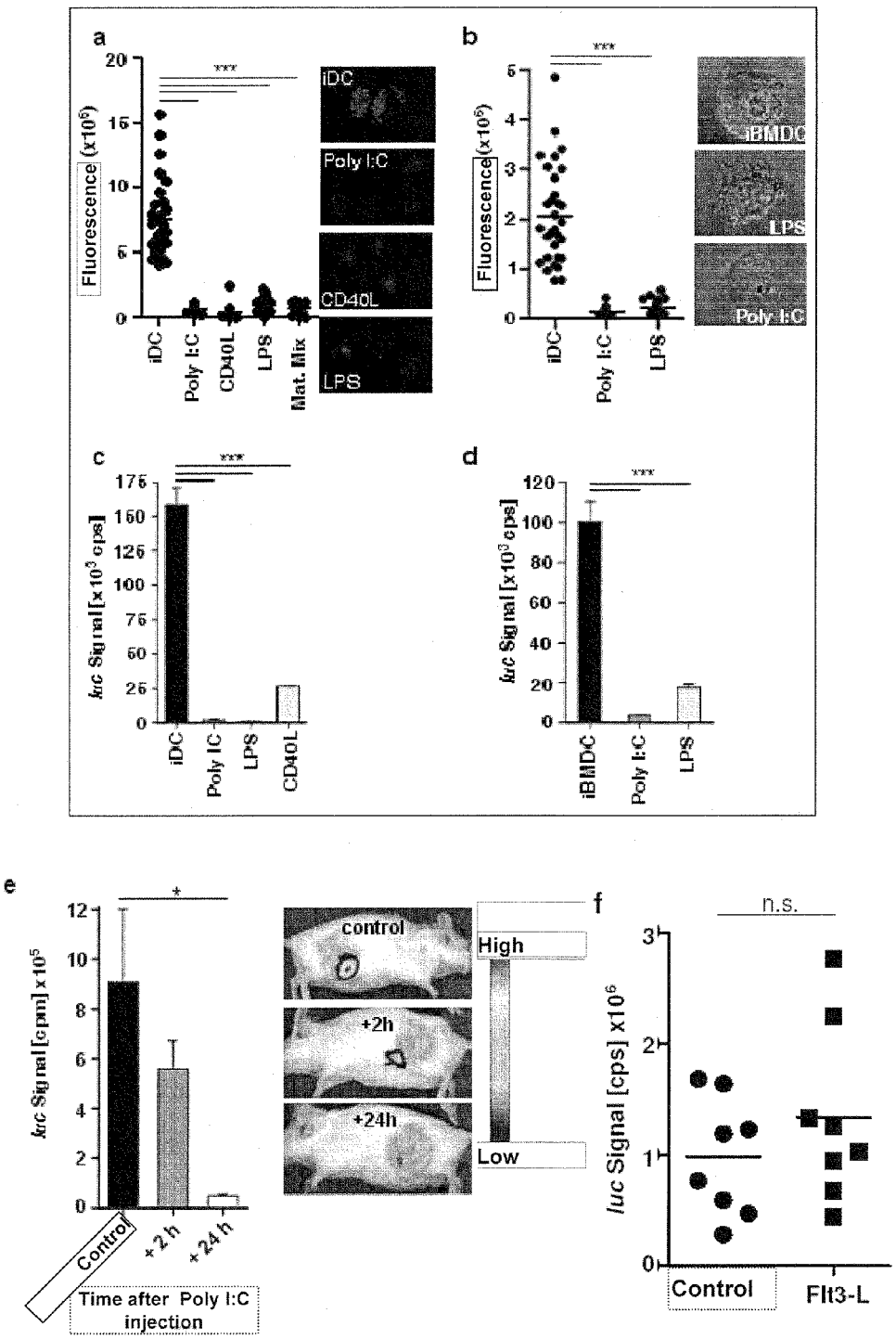

We matured human (FIG. 7(a, c)) and murine (FIG. 7(b, d)) DCs with various agents (Poly I:C (50 µg/ml), CD40L (1.0 ng/ml), LPS (20 ng/ml), Mat. Mix (TNFalpha (10 ng/ml), IL1b (10 ng/ml), PGE (1 µg/ml), IL6 (1000 U/ml)) for 40 hours. Then the cells were coincubated for 15 min with luciferase-RNA or Cy3-RNA. After culture for a further 22 h, RNA uptake was quantified in a luciferase test. The mean+SEM is shown. The iDCs coincubated with Cy3-RNA (red) were fixed with paraformaldehyde and counterstained (Hoechst 33342, blue). It was found, both in the quantification of Cy3-fluorescence and in the luciferase test, that after maturation of the iDCs, RNA uptake was reduced by more than 90%. These data are in agreement with published data, which show that the maturation of DCs leads to the down-regulation of macropinocytosis.

In order to verify to what extent maturing adjuvants can also lead in vivo to a reduction of RNA uptake, we tested the effect of Poly I:C on RNA uptake; cf. FIG. 7(e). For this, C57/Bl6 mice (n=4) were injected s.c. with PBS or Poly I:C (20 µg) and after 2 or 24 h, luciferase-RNA was applied intranodally. The in-vivo bioluminescence was measured after a further 24 h. The mean+SEM is shown. It was shown that there is a sharp reduction in RNA uptake, depending on the time interval after administration of the adjuvant. These data are in agreement with the observation that complete maturation of DCs takes approx. 24 h.

In contrast, Flt3-L administration does not have an inhibitory effect on RNA uptake in the lymph nodes. C57BL/6 mice (n=8) were treated i.p. on day 0 and 3 with 10 µg Flt3-L or were not treated in the control group. On day 10 the mice were injected intranodally with 20 µg luciferase-RNA. 24 h later the luciferase signal was measured by in-vivo bioluminescence. The graph in FIG. 7(f) shows the measured results for each individual mouse. The bars give the mean value of all measured values for a group. The experiment is representative for 3 independent experiments. Statistics: Student's t-test.

In addition, C57BL/6 mice (n=3-7) were administered Flt3L twice (day 0 and 3, each time 10 µg). On day 10 the lymph nodes were removed and the activation status (CD86, CD80, MHC-II, CD40) of the dendritic cells was determined by flow cytometry. We were able to show that the administration of Flt3L does not lead to maturation of the dendritic cells in the lymph node.

Example 7

Effects of Different Flt3L on the Cellular Composition in Lymph Nodes

In this experiment Flt3 ligand (Flt3-IgG4) was compared with commercially available Flt3 preparations with respect to the effect on different cell populations of the murine lymph node. A product recombinantly expressed in bacteria (Peprotech Flt3L; Peprotech, Hamburg, Germany) and a product expressed in human HEK293 cells (Humanzyme Flt3L, Humanzyme; Chicago Ill., U.S.A.) were used as commercially available Flt3 preparations. Human IgG4 (Sigma-Aldrich, Deisenhofen, Germany) served as control.

C57BL/6 mice (n=5) were injected intraperitoneally on day 0 Flt3L-IgG4, Flt3L (Humanzyme), Flt3L (Peprotech) or human IgG4 (Sigma-Aldrich) in an amount of 0.4 mol. On day 10 both inguinal lymph nodes of the mice were removed, the cell count determined by means of a Neubauer chamber and the cell populations were characterized by flow cytometry.

Figure 8:
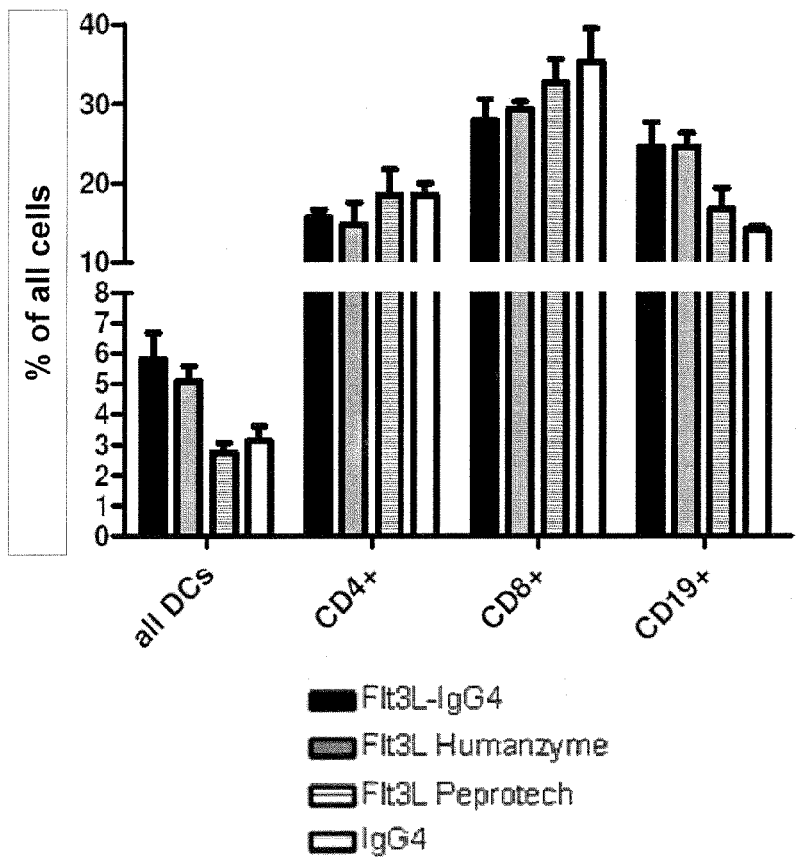
Figure 8:
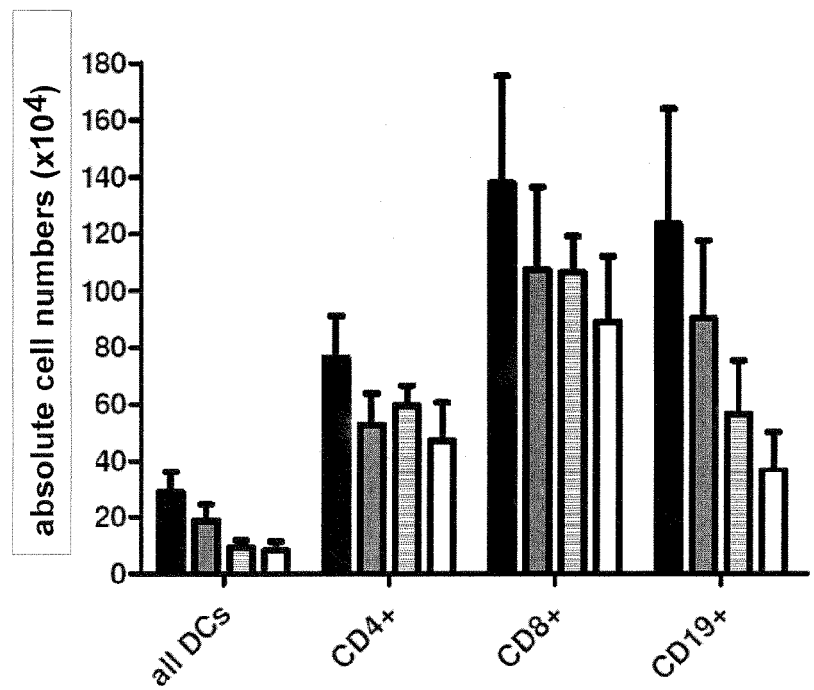

The different cell populations were defined by means of the following marker combinations: dendritic cells (DCs (marker: CD11c+/NK1.1−), CD4+ helper T cells (marker: CD3+/CD4+/CD8−/NK1.1−), CD8+ T cells (marker: CD3+/CD8+/CD4−/NK1.1−), CD19+ B cells (marker: CD19+/CD3−/NK1.1−). The antibodies for detecting the surface markers were obtained from Beckton Dickinson. FIG. 8 shows the frequency of dendritic cells (all DCs), CD4 positive, CD8 positive and CD19 positive cells in relation to the total number of cells prepared from the lymph node.

It was demonstrated that the effects induced by Flt3L-IgG4 were similar to those which were induced by the commercially available Flt3L products. Flt3L-IgG4 and Flt3L of Humanzyme had strong similarity with respect to the expansion of dendritic cells while Peprotech Flt3L was only slightly potent in this respect. Flt3L-IgG4 tended to be strongest regarding its effects on the expansion of the lymphocyte populations.

Example 8

Effects of Different Flt3L on the Stimulation of Naïve T Cells

In this experiment it was investigated to which extent the adjuvant function of Flt3L-IgG4 is equivalent to that of commercially available Flt3L products. To this end a product recombinantly expressed in bacteria (Peprotech Flt3L) and a product expressed in human HEK293 cells (Humanzyme Flt3L) was used; cf. Example 7. Human IgG4 served as control.

Naïve C57BL/6 mice (n=7) were injected intraperitoneally on day 0, +3 Flt3L (Flt3L-IgG4 or Flt3L (Humanzyme) or Flt3L (Peprotech)) or human IgG4 (Sigma) in an amount of 0.4 mol. These mice were immunized intralymphatically on day +7, +10 with 20 µg SIINFEKL coding RNA. The control group remained untreated (n=2). On day +15 the frequency of antigen-specific $CD8^+$ T lymphocytes was measured by flow cytometry in peripheral blood by means of MHC multimer measurement (Beckman Coulter).

The mice were administered intraperitoneally Flt3L in equimolar amounts (day 0, +3). In addition, mice were immunized intranodally twice with SIINFEKL coding RNA (+7, +10). The success of the immunization was quantified by flow cytometry on day +15 by means of tetramer staining.

Figure 9:
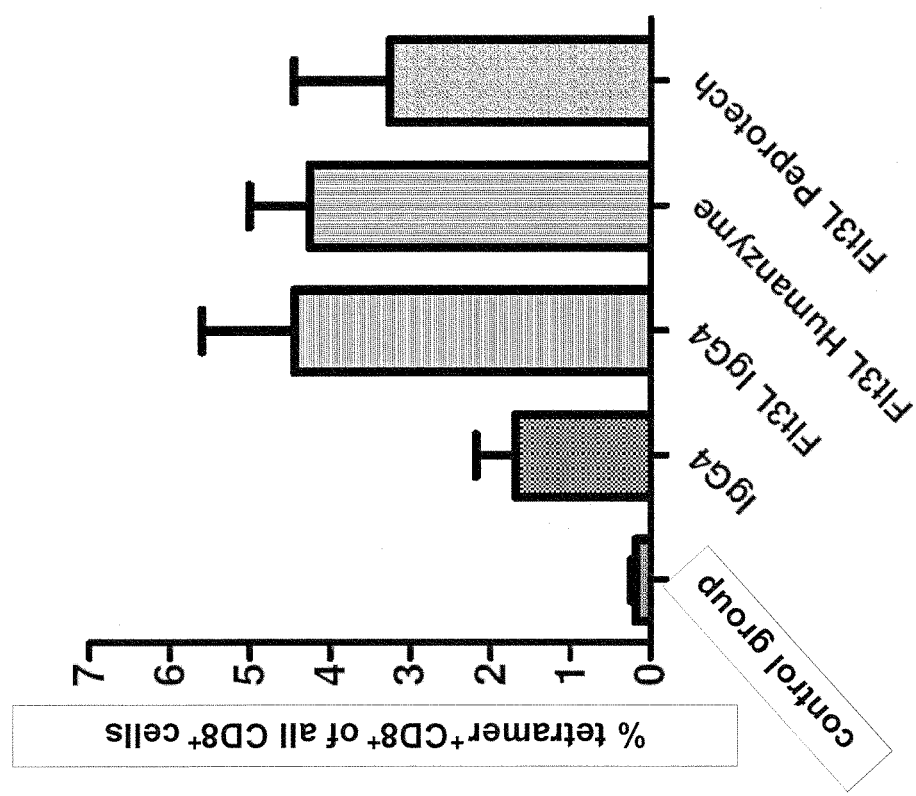

It was demonstrated that Flt3L-IgG4 as well as the commercially available Flt3L products had a significant adjuvant effect. The control group which was not immunized did not show any relevant frequency of tetramer positive T cells. Compared to the mice which were immunized without application of Flt3L the frequency of antigen-specific $CD8^+$ T lymphocytes was increased by a factor of 2-3. The use of Flt3L-IgG4 tended to provide the strongest effect (FIG. 9).

Example 9

Determination of the Half-Time of Flt3L-IgG4 in Serum

To determine the half-time of Flt3L-IgG4 in serum, two groups of Balb/c mice (n=3) were i.p. administered 20 µg and 50 µg, respectively, of Flt3L-IgG4. Serum samples obtained from the mice were preserved at defined time points (prior to administration; 3 h, 24 h, 48 h, 3 d, 5 d, 7 d, 9 d, 14 d, 21d). Human IgG was quantified in these samples by means of an ELISA assay. Due to the fusion of human IgG4 to Flt3L in this construct the Flt3L concentration can be determined by quantifying human IgG in serum of mice. The data demonstrate that following an initial maximum Flt3L is detectable after injection in serum of mice for up to 5 days. The calculated half-life for 50 µg Flt3L-IgG4 is 40 hours, the half-life (HL) for 20 µg is 51 hours.

In view of the published value for the half-life of Flt3L of 5 h (Robinson et al., 2003, BMT, 31:361-369), these values demonstrate an increased stability of Flt3L-IgG4 compared to Flt3L without IgG4 fusion (FIG. 10).

Example 10

Therapeutic Vaccination Against B16 Ova Tumors

To investigate the synergy of the combination of Flt3L administration together with RNA vaccination a therapeutic tumor experiment was performed. To this end four groups (n=10) of C57BL/6 mice were formed. All mice received on day 0 a s.c. injection of $2 \times 10^5$ B16 Ova tumor cells (Bellone et al., J. Immunol., 2000, 165:2651-2656). Thereof a control group was only treated by IgG4 injection (10 µg; d3, d7, d14, d17). A second control group only received injection of Flt3L-IgG4 (15 µg; d3, d7, d14, d17). The first therapy group was treated by intranodal injection of SIINFEKL coding RNA (20 µg; d11, d14, d17, d24) in combination with administration of IgG4 and the second therapy group received Flt3L-IgG4 as described above for RNA immunization.

It was demonstrated that the combination of Flt3L-IgG4 and intranodal vaccination of RNA has a synergistic effect. While in the case of RNA vaccination without Flt3L-IgG4 only ⅓ of the mice survived in the long term, the combination together with Flt3L-IgG4 can increase the portion of mice surviving in the long term to about 80%. Flt3L-IgG4 without RNA vaccination demonstrates a minimal therapeutic effect on tumor growth which however only results in a survival in the long term of 10% of the animals (FIG. 11).

Example 11

Therapeutic Vaccination Against B16 Ova Tumors

For confirming the synergistic effect of a combined administration of Flt3L and an RNA vaccine, a further therapeutic tumor experiment was performed. To this end four groups (n=10) of C57BL/6 mice were formed. All mice received on day 0 a s.c. injection of $2 \times 10^5$ B16 Ova tumor cells (Bellone et al., J. Immunol., 2000, 165:2651-2656). Thereof a control group was only treated by injection of IgG4 (15 µg; d3, d7, d14, d18). A second control group only received an injection of Flt3L-IgG4 (15 µg; d3, d7, d14, d18). A first therapy group was treated by intranodal injection of SIINFEKL coding RNA (20 µg; d10, d14, d18 and d21) in combination with administration of IgG4 and the second therapy group received Flt3L-IgG4 (Flt3L) for RNA immunization as described above. The tumor volume was determined on the following days after tumor inoculation: d7, d10, d13, d16, d19 and d22 (d=day).

It was demonstrated that the combination of Flt3L-IgG4 together with an intranodal vaccination of RNA has a synergistic effect. Only a slight delay of tumor growth was determined if only Flt3L was administered and also in the case of only RNA vaccination a progressive tumor growth was observed which, however, was decelerated. A complete suspension of tumor growth was only observed if Flt3L administration was combined with RNA vaccination (FIG. 12).

The invention claimed is:

1. An immunogenic preparation, which comprises: (i) isolated mRNA that codes for at least one antigen that induced an immune response in a mammal, and (ii) an immune response intensifying compound that consists of Fms-like tyrosine kinase 3 ligand (Flt3 ligand), wherein said Flt3 ligand is present in an amount effective to enhance the immune response induced by the at least one antigen by at least 10% as compared to an immune response elicited by the isolated mRNA without said immune response intensifying compound.

2. The immunogenic preparation as claimed in claim 1, wherein the isolated mRNA is synthetic.

3. The immunogenic preparation as claimed in claim 1, which further comprises at least one RNA-stabilizing factor.

4. A pharmaceutical composition that comprises an immunogenic preparation as claimed in claim 1 in a pharmaceutically compatible diluent or a pharmaceutically compatible vehicle, or both.

5. The pharmaceutical composition as claimed in claim 4 in the form of a formulation as a vaccine.

6. The pharmaceutical composition as claimed in claim 4 in the form of a formulation for intranodal administration.

* * * * *

SEQUENCE LISTING

<160> NUMBER OF SEQ ID NOS: 6

<210> SEQ ID NO 1
<211> LENGTH: 235

```
<212> TYPE: PRT
<213> ORGANISM: Homo sapiens

<400> SEQUENCE: 1

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
                20                  25                  30

Gln His Ser Pro Ile Ser Ser Asp Phe Ala Val Lys Ile Arg Glu Leu
                35                  40                  45

Ser Asp Tyr Leu Leu Gln Asp Tyr Pro Val Thr Val Ala Ser Asn Leu
            50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
                100                 105                 110

Phe Gln Pro Pro Pro Ser Cys Leu Arg Phe Val Gln Thr Asn Ile Ser
            115                 120                 125

Arg Leu Leu Gln Glu Thr Ser Glu Gln Leu Val Ala Leu Lys Pro Trp
130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro Pro Leu Leu Leu Leu Leu Leu Leu
            180                 185                 190

Pro Val Gly Leu Leu Leu Ala Ala Trp Cys Leu His Trp Gln
            195                 200                 205

Arg Thr Arg Arg Arg Thr Pro Arg Pro Gly Glu Gln Val Pro Pro Val
210                 215                 220

Pro Ser Pro Gln Asp Leu Leu Leu Val Glu His
225                 230                 235

<210> SEQ ID NO 2
<211> LENGTH: 232
<212> TYPE: PRT
<213> ORGANISM: Mus musculus

<400> SEQUENCE: 2

Met Thr Val Leu Ala Pro Ala Trp Ser Pro Asn Ser Ser Leu Leu Leu
1               5                   10                  15

Leu Leu Leu Leu Leu Ser Pro Cys Leu Arg Gly Thr Pro Asp Cys Tyr
                20                  25                  30

Phe Ser His Ser Pro Ile Ser Ser Asn Phe Lys Val Lys Phe Arg Glu
            35                  40                  45

Leu Thr Asp His Leu Leu Lys Asp Tyr Pro Val Thr Val Ala Val Asn
            50                  55                  60

Leu Gln Asp Glu Lys His Cys Lys Ala Leu Trp Ser Leu Phe Leu Ala
65                  70                  75                  80

Gln Arg Trp Ile Glu Gln Leu Lys Thr Val Ala Gly Ser Lys Met Gln
                85                  90                  95

Thr Leu Leu Glu Asp Val Asn Thr Glu Ile His Phe Val Thr Ser Cys
            100                 105                 110
```

Thr Phe Gln Pro Leu Pro Glu Cys Leu Arg Phe Val Gln Thr Asn Ile
                115                 120                 125

Ser His Leu Leu Lys Asp Thr Cys Thr Gln Leu Leu Gly Leu Lys Pro
    130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Pro Arg Ser Pro Ile Ala
                165                 170                 175

Leu Glu Ala Thr Glu Leu Pro Glu Pro Arg Pro Arg Gln Leu Leu Leu
            180                 185                 190

Leu Leu Leu Leu Leu Leu Pro Leu Thr Leu Val Leu Leu Ala Ala Ala
        195                 200                 205

Trp Gly Leu Arg Trp Gln Arg Ala Arg Arg Arg Gly Glu Leu His Pro
    210                 215                 220

Gly Val Pro Leu Pro Ser His Pro
225                 230

<210> SEQ ID NO 3
<211> LENGTH: 1056
<212> TYPE: DNA
<213> ORGANISM: Homo sapiens

<400> SEQUENCE: 3
tctctggctg tcacccggct tggcccccttc cacacccaac tggggcaagc ctgacccggc      60
gacaggaggc atgaggggcc cccggccgaa atgacagtgc tggcgccagc tggagccca     120 acaacctatc tcctcctgct gctgctgctg agctcgggac tcagtgggac ccaggactgc    180
tccttccaac acagccccat ctcctccgac ttcgctgtca aaatccgtga gctgtctgac    240
tacctgcttc aagattaccc agtcaccgtg gcctccaacc tgcaggacga ggagctctgc    300
gggggcctct ggcggctggt cctggcacag cgctggatgg agcggctcaa gactgtcgct    360
gggtccaaga tgcaaggctt gctggagcgc gtgaacacgg agatacactt tgtcaccaaa    420
tgtgcctttc agcccccccc cagctgtctt cgcttcgtcc agaccaacat ctcccgcctc    480
ctgcaggaga cctccgagca gctggtggcg ctgaagccct ggatcactcg ccagaacttc    540
tcccggtgcc tggagctgca gtgtcagccc gactcctcaa ccctgccacc ccatggagt     600 cccccggcccc tggaggccac agccccgaca gccccgcagc cccctctgct cctcctactg    660
ctgctgcccg tgggcctcct gctgctggcc gctgcctggt gcctgcactg gcagaggacg    720
cggcggagga caccccgccc tggggagcag gtgcccccg tccccagtcc ccaggacctg    780
ctgcttgtgg agcactgacc tggccaaggc ctcatcctgg ggaggatact gaggcacaca    840
gaggggagtc accagccaga ggatgcatag cctggacaca gaggaagttg ctagaggcc    900 ggtcccttcc ttgggcccct ctcattccct ccccagaatg gaggcaacgc cagaatccag    960
caccggcccc atttacccaa ctctgtacaa agcccttgtc cccatgaaat tgtatataaa   1020
tcatcctttt ctaccaaaaa aaaaaaaaaa aaaaaa                              1056

<210> SEQ ID NO 4
<211> LENGTH: 1152
<212> TYPE: DNA
<213> ORGANISM: Mus musculus

<400> SEQUENCE: 4
gaattcgcgg ccgcgtcgac attctgggga cgtcggtcgg ggttcttaga agaggagatg      60
acttttcaca gtcactgagg ctcgtgcagg aagcctgggg gagcaggagg cggaaaccga    120

```
cccacatcaa gggcggcagg gccgggcggc ggggtacagg ggttgggggg aagggggctg      180
cagggtatga gcccgagacc tgccctcctg tcacttccaa gaacctgtca caggcatgag      240
gggtccccgg cagagatgac agtgctggcg ccagcctgga gcccaaattc ctccctgttg      300
ctgctgttgc tgctgctgag tccttgcctg cgggggacac ctgactgtta cttcagccac      360
agtcccatct cctccaactt caaagtgaag tttagagagt tgactgacca cctgcttaaa      420
gattacccag tcactgtggc cgtcaatctt caggacgaga agcactgcaa ggccttgtgg      480
agcctcttcc tagcccagcg ctggatagag caactgaaga ctgtggcagg gtctaagatg      540
caaacgcttc tggaggacgt caacaccgag atacattttg tcacctcatg taccttccag      600
cccctaccag aatgtctgcg attcgtccag accaacatct cccacctcct gaaggacacc      660
tgcacacagc tgcttggtct gaagccctgt atcgggaagg cctgccagaa tttctctcgg      720
tgcctggagg tgcagtgcca gccggactcc tccaccctgc tgccccaag gagtcccata      780 gccctagaag ccacggagct cccagagcct cggcccaggc agctgttgct cctgctgctg      840
ctgctgctgc tctcacact ggtgctgctg gcagccgcct ggggccttcg ctggcaaagg      900
gcaagaagga gggggagct ccaccctggg gtgcccctcc cctcccatcc ctaggatgcg      960
agccttgtgc atcgttgact cagccagggt cttatctcga tgaggtctca atatgttgcc    1020
caaactgact ttgaaaacct cgatgcacct tcctgcccca caaacttcca acagctgggg    1080
cttacgggca tgctatatac aacaaggctt tcttttcttc tttcttggtg ctagagttgg    1140
gaaccaaaac aa                                                         1152
```

<210> SEQ ID NO 5
<211> LENGTH: 224
<212> TYPE: PRT
<213> ORGANISM: Homo sapiens

<400> SEQUENCE: 5

```
Pro Pro Cys Pro Ser Cys Pro Ala Pro Glu Phe Leu Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser Gln Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Gly Leu Pro Ser Ser Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Gln Glu Glu Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Arg Leu Thr Val Asp Lys Ser
```

```
                    180                 185                 190
Arg Trp Gln Glu Gly Asn Val Phe Ser Cys Ser Val Met His Glu Ala
                195                 200                 205

Leu His Asn His Tyr Thr Gln Lys Ser Leu Ser Leu Ser Pro Gly Lys
        210                 215                 220

<210> SEQ ID NO 6
<211> LENGTH: 411
<212> TYPE: PRT
<213> ORGANISM: Artificial
<220> FEATURE:
<223> OTHER INFORMATION: Fusionsprotein

<400> SEQUENCE: 6

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
                20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
        50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro Pro Arg Ser Pro Pro Cys Pro Ser
            180                 185                 190

Cys Pro Ala Pro Glu Phe Leu Gly Gly Pro Ser Val Phe Leu Phe Pro
        195                 200                 205

Pro Lys Pro Lys Asp Thr Leu Met Ile Ser Arg Thr Pro Glu Val Thr
    210                 215                 220

Cys Val Val Val Asp Val Ser Gln Glu Asp Pro Glu Val Gln Phe Asn
225                 230                 235                 240

Trp Tyr Val Asp Gly Val Glu Val His Asn Ala Lys Thr Lys Pro Arg
                245                 250                 255

Glu Glu Gln Phe Asn Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Gly Leu Pro Ser Ser Ile Glu Lys Thr Ile Ser Lys Ala Lys
    290                 295                 300

Gly Gln Pro Arg Glu Pro Gln Val Tyr Thr Leu Pro Pro Ser Gln Glu
305                 310                 315                 320

Glu Met Thr Lys Asn Gln Val Ser Leu Thr Cys Leu Val Lys Gly Phe
```

-continued

```
                325                 330                 335
Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Tyr Ser Arg Leu Thr Val Asp Lys Ser Arg Trp Gln Glu Gly
    370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410
```